United States Patent [19]

Magota et al.

[11] Patent Number: 4,987,070
[45] Date of Patent: Jan. 22, 1991

[54] USE OF A 97 AMINO ACID LEADER SEQUENCE FROM THE E. COLI B-GALACTOSIDASE GENE FOR THE PRODUCTION OF HANP AND HPTC AS FUSION PROTEINS

[75] Inventors: Koji Magota, Osaka; Takehiro Oshima, Tochigi; Shoji Tanaka, Hyogo, all of Japan

[73] Assignee: Suntory Limited, Osaka, Japan

[21] Appl. No.: 163,548

[22] Filed: Mar. 3, 1988

[30] Foreign Application Priority Data

Mar. 4, 1987 [JP] Japan .................................. 62-47796

[51] Int. Cl.$^5$ ............................................. C12P 21/02
[52] U.S. Cl. .................................. 435/69.7; 435/69.8; 435/69.7
[58] Field of Search ...................... 435/68, 172.3, 69.6, 435/69.7, 69.8, 71.1; 530/326, 253, 350, 324, 326, 253, 350

[56] References Cited

U.S. PATENT DOCUMENTS

| 4,431,739 | 2/1984 | Riggs | 435/253 |
| 4,549,986 | 10/1985 | Evans | 260/112.5 T |
| 4,673,732 | 6/1987 | Kiso | 530/326 |
| 4,736,023 | 4/1988 | Evans | 536/27 |
| 4,743,679 | 5/1988 | Cohen | 530/350 |
| 4,769,326 | 9/1988 | Rutter | 435/68 |

FOREIGN PATENT DOCUMENTS

| 0001930 | 5/1979 | European Pat. Off. |
| 0035384 | 9/1981 | European Pat. Off. |
| 0077569 | 4/1983 | European Pat. Off. |
| 0109748 | 5/1984 | European Pat. Off. |
| 121352 | 10/1984 | European Pat. Off. |
| 0128733 | 12/1984 | European Pat. Off. |
| 0286956 | 10/1988 | European Pat. Off. |
| 62-6689 | 1/1987 | Japan . |
| 8403103 | 8/1984 | PCT Int'l Appl. |
| 2140810 | 12/1984 | United Kingdom . |
| 8515686 | 6/1985 | United Kingdom . |
| 8600754 | 1/1986 | United Kingdom . |
| 8403519 | 9/1984 | World Int. Prop. O. |

OTHER PUBLICATIONS

Nagai K. and Thogersen H. C. 1984 Nature 309 : 810–812.

(List continued on next page.)

Primary Examiner—Richard A. Schwartz
Assistant Examiner—John D. Ulm
Attorney, Agent, or Firm—Burns, Doane, Swecker & Mathis

[57] ABSTRACT

A process for the production of a physiologically active peptide (a target peptide) containing cysteine residue, comprising the steps of:

(1) culturing Escherichia coli transformed with a plasmid capable of expressing a fusion protein under control of a promoter of E. coli origin or a promoter of a phage origin, wherein the fusion protein is represented by the following formula:

A—L—B wherein B represents a target peptide containing cysteine residue; A represents a partner polypeptide consisting of 90 to 220 amino acid residue but not containing cysteine residue; and L represents a linker amino acid residue positioned between C-terminal of the partner polypeptide and N-terminal of the target peptide wherein the same amino acid as the linker amino acid is not present in the target peptide, and the linker amino acid is selected so that the peptide bond between the C-terminal of the linker amino acid and the N-terminal of the target peptide is claimed by a protease or the linker amino acid is selectively degraded by a chemical substance;

(2) disrupting the cultured cells and obtaining an insoluble fraction containing the fusion protein;

(3) solubilizing the fusion protein with a solubilizing agent, and treating the solubilizing fusion protein with the protease or the chemical substance to liberate the target peptide, and isolating the target peptide.

6 Claims, 20 Drawing Sheets

OTHER PUBLICATIONS

Winkler M. E. et al., Mar. 1987, J. Cell. Biochem, 11C; 221.
Chenyl, L. et al. 1985 DNA 4(1): 91.
Edbrook M. R. et al. 1985 Embo J. 4 (3) 715–724.
Bielka, H. et al. 1979 *Enzyme Nomenclature*, Academic Press, N.Y., 1979; p. 330.
Zoller et al 1982 Nucleic Acids Research Volume 10(20) 6487–6500.
Y. Yoshitoshi, *Taisha*, vol. 22, No. 6, pp. 499–504 (1985).
Y. Saito et al., *J. Biochem.*, 102, pp. 111–122 (1987).
K. Itakura et al., *Science*, vol. 198, pp. 1056–1063 (1977).
Li-He Guo et al., *Gene*, 29, pp. 251–254 (1984).
K. Kangawa et al., *Nature*, vol. 313, pp. 397–400 (1985).
K. Kangawa et al., *Biochem. Biophys. Res. Commun.*, vol. 118, No. 1, pp. 131–139 (1984).
Goeddel, *Proc. Natl. Acad. Sci. U.S.A.*, vol. 76, No. 1, pp. 106–110 (1979).
J. Shine et al., *Nature*, vol. 285, pp. 456–461 (1980).
S. Oikawa, *Nature*, vol. 309, pp. 724–726 (1984).

LANE 1 MOLECULAR WEIGHT STANDARD

LANE 2 EXPRESSION PRODUCT FROM pGHα97(Ser)rop⁻

LANE 3 EXPRESSION PRODUCT FROM pGHα97S

M  MOLECULAR WEIGHT STANDARD
T  EXPRESSION PRODUCT IN CELL DISRUPTANT
S  EXPRESSION PRODUCT IN SUPERNATANT
P  EXPRESSION PRODUCT IN PRECIPITATE

| LANE | AMOUNT OF API ENZYME USED |
|------|---------------------------|
| 1 | 0 ng API/μg αhANP |
| 2 | 5 ng API/μg αhANP |
| 3 | 1 ng API/μg αhANP |
| 4 | 0.2 ng API/μg αhANP |

USE OF A 97 AMINO ACID LEADER SEQUENCE FROM THE E. COLI B-GALACTOSIDASE GENE FOR THE PRODUCTION OF HANP AND HPTC AS FUSION PROTEINS

BACKGROUND OF THE INVENTION

1. Field of the Invention

The present invention relates to a process for the production of a physiologically active peptide containing at least one cysteine residue (hereinafter abbreviated as target peptide).

2. Description of the Related Art

There have been many attempts to obtain physiologically active peptides or proteins of eukaryote origin in microbial cells such as *Escherichia coli* cells using recombinant DNA techniques.

To produce a relatively small size peptide which is readily degraded in microbial cells such as *E. coli*, a process is usually used wherein a desired peptide or protein is produced in microbial cells as a protein fusion with another peptide or protein, the produced fusion protein is then chemically or enzymatically cleaved to liberate the desired peptide or protein, and the desired peptide and protein is isolated and purified.

Various methods are known for liberating a desired peptide from a fusion protein. In the case of a desired peptide not containing a methionine residue, the desired peptide is produced as a fusion protein wherein the desired peptide is fused with a partner protein via a methionine residue, and the desired peptide is liberated from the partner protein by cleavage at the methionine residue with cyanogen bromide (Science, 198, 1059 (1977); and Proc. Natl. Acad. Sci. USA, 76, 106 (1978)). In the case of a desired peptide not containing an arginine or lysine residue, the desired peptide is produced as a fusion protein wherein the desired peptide is fused with a partner protein via the arginine or lysine residue, and the desired peptide is liberated from the partner protein by proteolytic cleavage at the arginine or lysine residue with trypsin, which specifically cleaves a peptide bond at the C-terminal of the arginine or lysine residue (Nature, 285, 456, 1980). Moreover, in some cases, Achromobacter protease I (hereinafter abbreviated as API, also known as lysyl endopeptidase), which specifically cleaves a peptide bond at the C-terminal of a lysine residue, may be used.

In many cases, a partner protein which forms a fusion protein in combination with a desired peptide is selected from a protein which is naturally produced by a host organism. In this case, usually, a polypeptide fragment having an appropriate size derived from the N-terminal part of a protein which is produced in large amounts by the host is used as a partner protein. In such a case, it is considered that the size of the partner protein affects the productivity of the desired peptide. For example, although it is thought that by using a smaller size of a partner protein a larger amount of a desired peptide is obtained, because of a high proportion of the desired peptide in the fusion protein. This does not always occur. For example, in the case of production of insulin using *E. coli* β-galactosidase as a partner in a fusion protein, although a decrease of the size of the β-galactosidase region provides an increase in the production of the target insulin, a further decrease of the β-galactosidase size decreases the production of the target insulin (Gene, 29, 251, 1984). As seen from the above, when a particular peptide is to be produced as a fusion protein, there is no rule determining a size of a partner protein which provides maximum productivity of a desired peptide.

Therefore, the most important point for efficient production of a target peptide is the selection of the most suitable partner protein for the target peptide efficiently to express a fusion protein of the target peptide and the partner protein, and efficiently recover the target peptide from the fusion protein. However, since a general rule for such a selection has not been established, the optimum conditions for a particular target peptide must be found by experiment.

Next, as examples of a target peptide containing cysteine residues, α-type human atrial natriuretic polypeptide (hereinafter abbreviated as α-hANP), and human calcitonin precursor (hereinafter abbreviated as HPTC) are mentioned, and the problems in the production of the these peptides by the recombinant DNA technique are described in detail.

The α-hANP is a peptide consisting of 28 amino acid residues, containing two cysteine residues at portions 7 and 23 which form an intramolecular disulfide bond, and having the following formula (I):

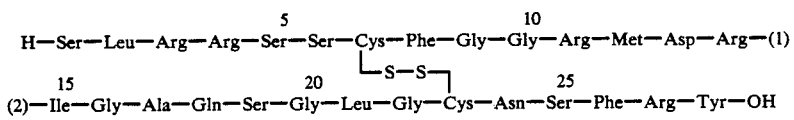

wherein (1) and (2) are directly bonded.

The α-hANP was extracted and purified from human atria by Matsuo and Kangawa (European Patent Publication No. 0147193). The α-hANP exhibits a notable natriuretic activity and blood pressure lowering activity (Biochem. Biophys. Res. Commun. 118, 131-139, 1984).

On the other hand, the HPCT is a peptide consisting of 36 amino acid residues, containing two cysteine residues at positions 1 and 7 which form an intramolecular disulfide bond, and having the following formula (II):

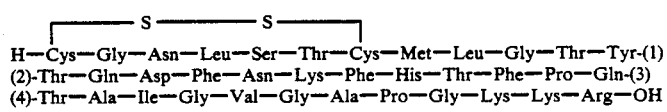

wherein (1) is directly bonded with (2), and (3) is directly bonded with (4).

The HPCT is known as an intermediate of human calcitonin corresponding to a sequence from the first amino acid to the 32nd amino acid in the formula (II) (Nature 295 345-347, 1982).

Although these peptides are now chemically synthesized, the process for chemical synthesis of a large amount of these peptide is labor intensive and time-consuming. Therefore, since these peptide in particular are intended for use as pharmaceuticals, a simple and inexpensive process for large scale production of these peptides is strongly desired.

To resolve the above-mentioned problems, attempts have been made to produce such peptides using a recombinant DNA technique. For example, to produce α-hANP, α-hANP is expressed as a fusion protein comprising the α-hANP and E. coli Trp E protein, and a crude extract containing the fusion protein prepared from a cell disruptant is treated with lysyl endopeptidase or a coagulation factor Xa to liberate the α-hANP from the fusion protein (Seikagaku, 57(8), 854(1984). In this procedure, however, the recovery process is complicated and the recovery ratio of the target peptide from the fusion protein is low, and thereofor, this procedure is not practical. To resolve the problem, the present inventors invented a process to produce a physiologically active peptide not containing lysine residues represented by α-hANP. The target peptide is expressed as a fusion protein comprising the target peptide and a partner polypeptide of 90 to 220 amino acid residues not containing lysine residues linked via a lysine residue, and the fusion protein is treated with lysyl endopeptidase to liberate the target peptide (Japanese Patent Application No. 61-101100). However, this improved process does not provide a satisfactory recovery efficiency of the target peptide.

On the other hand, for the production of the HPCT, the present inventors reported a process for the production of a derivative of HPCT wherein the eighth methionine residue is converted to valine residue in the formula (II) (Japanese Patent Application No. 58-203953). In this process, the target peptide is expressed as a fusion peptide with E. coli alkaline phosphatase, and then the fusion protein is treated by cyanogen bromide to obtain the target peptide. However, this process, as described for α-hANP, also does not have a satisfactory recovery efficiency of the target peptide from the fusion protein. In contrast to these cases, it is known that, in the production of a peptide not containing cysteine residues by a recombinant DNA technique, the recovery efficiency of the target peptide from fusion protein is higher than the case of a target peptide containing cysteine residue(s). Therefore, a key factor in the efficient production of a peptide containing cysteine residue(s) is an increase of the recovery efficiency of the target peptide from the fusion protein. A solution to this problem is strongly desired at this time.

Therefore, the present invention is intended to provide a process which can be applied to a large scale production of a peptide containing cysteine residue(s), and especially, relates to the selection of a partner protein and a linker amino acid which bond the partner protein and the target peptide in fusion protein.

SUMMARY OF THE INVENTION

The present inventors studied in detail the reasons for the drawback of the prior art, and found that, in the case of a fusion protein comprising a desired peptide and a partner protein both containing cysteine residues, a disulfide bond is formed between the cysteine residue in the desired peptide and the cysteine residue in the partner protein resulting in a lower yield of the desired peptide, and found that, by using a partner protein not containing any cysteine residues, the problem can be resolved.

Therefore, the present invention provides a process for the production of a physiologically active peptide (a target peptide) containing cysteine residues, comprising the steps of:

(1) culturing *Escherichia coli* transformed with a plasmid capable of expressing a fusion protein under control of a promoter of *E. coli* origin or a promoter of a phage origin, wherein the fusion protein is represented by the following formula:

A—L—B

wherein B represents a target peptide containing cysteine residues; A represents a partner polypeptide consisting of 90 to 220 amino acid residues but not containing any cysteine residue; and L represents a linker amino acid residue positioned between a C-terminal of the partner polypeptide and an N-terminal of the target peptide, wherein the same amino acid as the linker amino acid is not present in the target peptide and the linker amino acid is selected so that the peptide bond between C-terminal of the linker amino acid and N-terminal of the target peptide is cleaved by a protease or the linker amino acid is selectively degraded by a chemical substance;

(2) disrupting the cultured cells and obtaining an insoluble fraction containing the fusion protein;

(3) solubilizing the fusion protein with a solubilizing agent, and treating the solubilized fusion protein with the protease or the chemical substance to liberate the target peptide, and isolating the target peptide.

The present invention also provides a physiologically active peptide produced by the above-mentioned process.

DESCRIPTION OF THE PREFERRED EMBODIMENT

Figure 1:
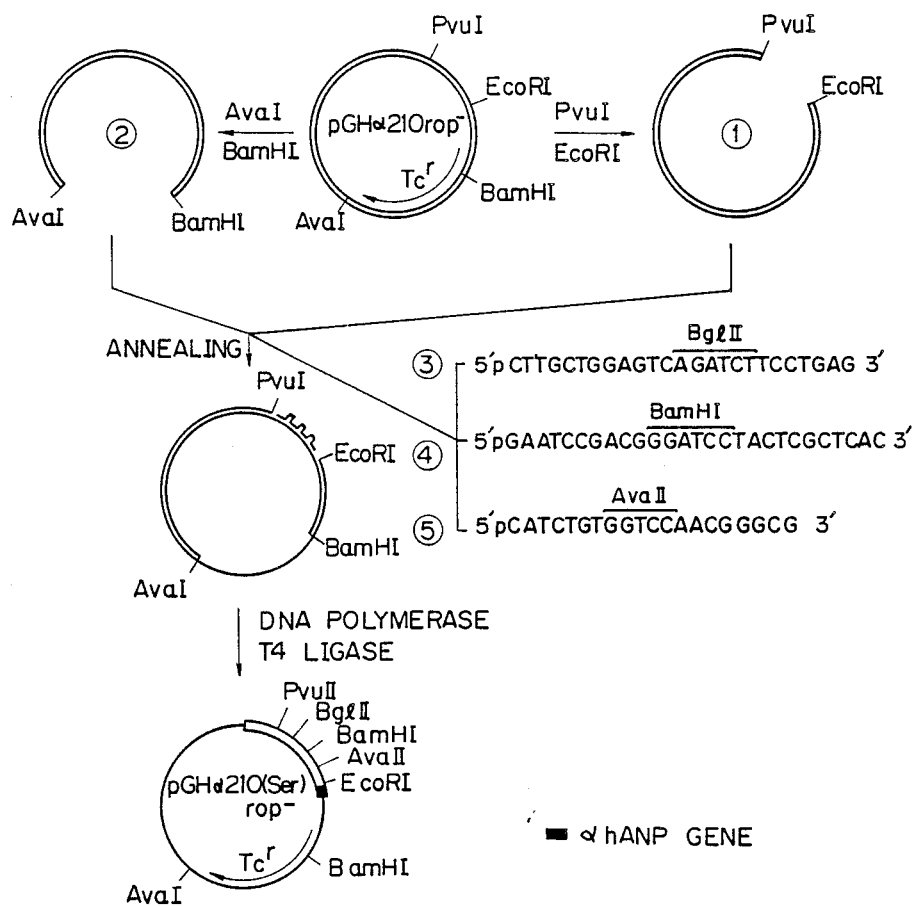
FIG. 1 represents a process for the construction of an expression plasmid pGHα210(Ser)rop⁻ for a fusion protein comprising α-hANP as a target peptide and βgal 210(Ser) as a partner protein. The βgal 210(Ser) is a derivative of a βgal 210 protein wherein cysteine residues are replaced by serine residues.

The present invention is applicable to processes for the production of any physiologically active peptides containing at least one cysteine residue. Such peptides include, in addition to the α-hANP and the HPCT explained in detail herein, insulin A chain and B chain, calcitonin precursor of other than human origin, somatostatin, and the like.

A partner protein is any protein not containing cysteine residues. Such proteins include natural proteins and a part thereof containing no cysteine residues, and modified proteins wherein cysteine residues in natural proteins or a part thereof are deleted or converted to other amino acid residues. The partner protein can contain, in addition to the above-mentioned protein, a few, for example 1 to 5, additional amino acids. The example is polypeptides comprising 90 to 220 amino acid residues of E. coli β-galactosidase. Particular embodiments of the partner protein include a polypeptide consisting of a polypeptide of E. coli β-galactosidase protein from the first amino acid at the N-terminal to 210th amino acid calculated from the N-terminal amino acid and two additional amino acids such as glutamic acid and phenylalanine; a polypeptide consisting of a polypeptide of E. coli β-galactosidase from the first amino acid at the N-terminal to 97th amino acid calculated from the N-terminal amino acid and two additional amino acid residues such as glutamine and phenylalanine; and a polypeptide consisting of a polypeptide of E. coli β-galactosidase from the first amino acid at the N-terminal to 97th amino acid calculated from the N-terminal amino acid and three additional amino acid residues such as glutamic acid, phenylalanine and leucine.

These additional amino acids are introduced, for example, during the recombinant DNA manipulation as an amino acid encoded by a linker DNA.

However, since the natural form of these polypeptides contains cysteine residues, the cysteine residues must be deleted or replaced by other amino acids. This is easily carried out by site-directed mutagenesis. Any amino acid can be used for the replacement of the cysteine residues, but preferably serine is used. Note, lysine is not preferable. Since the above-mentioned polypeptides in natural form from E. coli β-galactosidase protein do not contain lysine residues, when a fusion protein comprising a target peptide and partner polypeptide is cleaved with lysyl endopeptidase, the partner polypeptide is not cleaved on the inside and, therefore, the target peptide can be easily isolated and purified.

According to the present invention, a physiologically active peptide, i.e., a target peptide, is expressed as a fusion protein wherein the C-terminal of the partner polypeptide is linked with the N-terminal of target peptide via a linker amino acid residue. The linker amino acid is preferably lysine, arginine, glutamic acid, or methionine. When lysine is used as a linker amino acid, the peptide bond between a target peptide and the linker lysine is proteolytically cleaved with, for example, lysyl endopeptidase to liberate the target peptide. When arginine is used as a linker amino acid, the peptide bond between a target peptide and the linker arginine is proteolytically cleaved with, for example, clostripain to liberate the target peptide. When glutamic acid is used as a linker amino acid, the peptide bond between a target peptide and the linker glutamic acid is proteolytically cleaved with, for example, protease V$_8$ to liberate the target peptide. On the other hand, when methionine is used as a linker amino acid, the linker methionine is degraded with cyanogen bromide to liberate the target peptide from the partner protein.

A fusion protein is expressed by a gene comprising a DNA coding for a partner protein such as a β-gal fragment linked in a reading frame with a DNA coding for a target peptide via a synthetic double stranded oligonucleotide linker containing a codon for a linker amino acid such as lysine or glutamic acid. In this case, the oligonucleotide linker preferably contains a DNA sequence coding for a part of the N-terminal of the target peptide immediately downstream of the codon for the linker amino acid such as lysine or glutamic acid lysine, and has appropriate restriction sites at both terminals thereof.

The gene coding for β-galactosidase is derived from, for example, plasmid paNE2, which contains a β-galactosidase gene under a lac promoter. A gene coding for α-hANP, a target peptide, is derived from, for example a gene coding for γ-hANP, which is a precursor of α-hANP, which gene is contained in plasmid pS224-3 (European Patent Publication No. 0164 273).

The gene coding for HPCT is derived from, for example, plasmid pAHPC38.

The promoter used to efficiently express a fusion protein gene may be any promoter of a gene for a protein produced in a large amount in *E. coli* or of phages. According to the present invention, a Lac promoter derived from *E. coli* lactose gene, an lpp promoter derived from *E. coli* outer membrane lipoprotein gene, and a $P_L$ promoter derived from the λ phage gene are preferable. These promoters can be easily obtained from known plasmids according to conventional recombinant DNA techniques. For example, according to the present invention, a $P_L$ promoter is obtained from a plasmid pP$_L$lacZ'210αhANP (FIG. 8); and an lpp promoter is obtained from a plasmid pIN5T4 (FIG. 9). These plasmids are described in Japanese Patent Application No. 61-101100 and No. 61-132186. The plasmid pP$_L$lacZ'210αhANP was derived from plasmid pS20. *E. coli* (N4830/pS20) containing plasmid pS20 was deposited with the Fermentation Research Institute Agency of Industrial Science and Technology (FRI), Higashi 1-1-3, Tsukuba-shi, Ibaraki, Japan, on May 31, 1984 as FERM BP-535, under the Budapest Treaty. The plasmid pIN5T4 was derived from a plasmid pINI-A2. *E. coli* (JA221/pINI-A2) containing a plasmid pINI-A2 and was deposited with the FRI on July 18, 1983 as FRM BP-320.

A fusion protein of the present invention can be expressed at a high efficiency by using an expression plasmid wherein an attenuator terminator of tryptophan operon (trp a) is inserted immediately downstream of a structural gene for the fusion protein. For example, as shown in Examples and FIG. 4, the introduction of the trp a into plasmid pGHα97(Ser)rop$^-$ immediately downstream of α-hANP structural gene results in the formation of a plasmid pGHα97S, and the productivity of the desired fusion protein is greatly increased.

Gene coding for a target physiologically active peptide can be chemically synthesized. Alternatively, it can be cDNA prepared from mRNA obtained from cells which produce the target peptide or a precursor thereof.

According to the present invention, gene coding for α-hANP is obtained from plasmids pGHα210rop$^-$ and pGHα439rop$^-$ which contain the α-hANP gene with the lac promoter. The processes for the construction of these plasmids are described in detail in Reference Examples 1 to 3.

The method of cleavage between a target peptide region and a partner protein region in a fusion protein depends on the nature of a linker amino acid connecting both regions. When using lysine as a linker amino acid, lysyl endopeptidase, which splits the C-terminal of lysine residure, is used. Preferably, Achromobacter protease I (API) derived from *Achromobacter lyticus* is used. This Enzyme is commercially available from Wako Junyaku, Japan.

To obtain a target peptide, E. coli transformed with an expression plasmid containing a gene coding for a fusion protein comprising the target peptide and an appropriate partner protein is cultured in an appropriate medium, and the expression of the fusion protein is induced. Cells of the *E. coli* are then collected and the cells are disrupted. Centrifugation of the disruptant provides a precipitate containing the fusion protein. This method is advantageous in that most of contaminant proteins and peptides remain in the supernatant. The precipitate is then preferably treated with 5 to 10 M urea to solubilize the fusion protein. The use of urea is advantageous over other solubilizing agents such as sodium dodecyl sulfate (SDS) in that urea does not inhibit the enzyme API. After solubilization of the fusion protein with urea such as 8 M urea, the treated mixture is diluted with an appropriate buffer, and API is added to the mixture to cleave the fusion protein, resulting in the liberation of the target peptide. The liberated target peptide is isolated and purified according to conventional procedures for purification of a peptide or protein.

According to the present invention, since the partner protein in the fusion protein does not contain cysteine residues, a disulfide bond between the partner protein and target protein is not formed. Therefore, the target peptide is isolated from the partner protein in very high yield. Moreover, in an embodiment of the present process wherein the partner protein does not contain lysine residues, cleavage of the fusion protein with lysyl endopeptidase such as API does not provide simultaneous cleavage within the partner protein. Therefore, the target peptide can be very easily isolated and purified.

Moreover, according to the present invention, since the size of the partner protein is controlled to within 90 to 220 amino acid residues, a proportion of the target protein in a fusion protein is high while maintaining the stability of the fusion protein, and therefore of the target peptide, in host cells.

Finally, according to the present process, since the desired fusion protein is first recovered in a undissolved fraction, i.e., precipitate from cell disruptant, and the fusion protein is extracted from the undissolved fraction, impure proteins are effectively eliminated. Moreover, when using an enzyme such as API to liberate the target peptide, this step can be carried out without further purification of the fusion protein. These procedures provide the efficient and simple production of the target peptide.

EXAMPLES

The present invention will now be further illustrated by but is by no means limited to the following examples.

First, processes for construction of plasmids pGHα210rop$^-$, pGHα439rop$^-$, and pP$_L$lacZ'2-10αhANP containing DNA coding for fusion protein comprising α-hANP as a target peptide and a part of native β-galactosidase protein still containing cysteine residues are described in Reference Examples 1 to 5.

Figure 11:
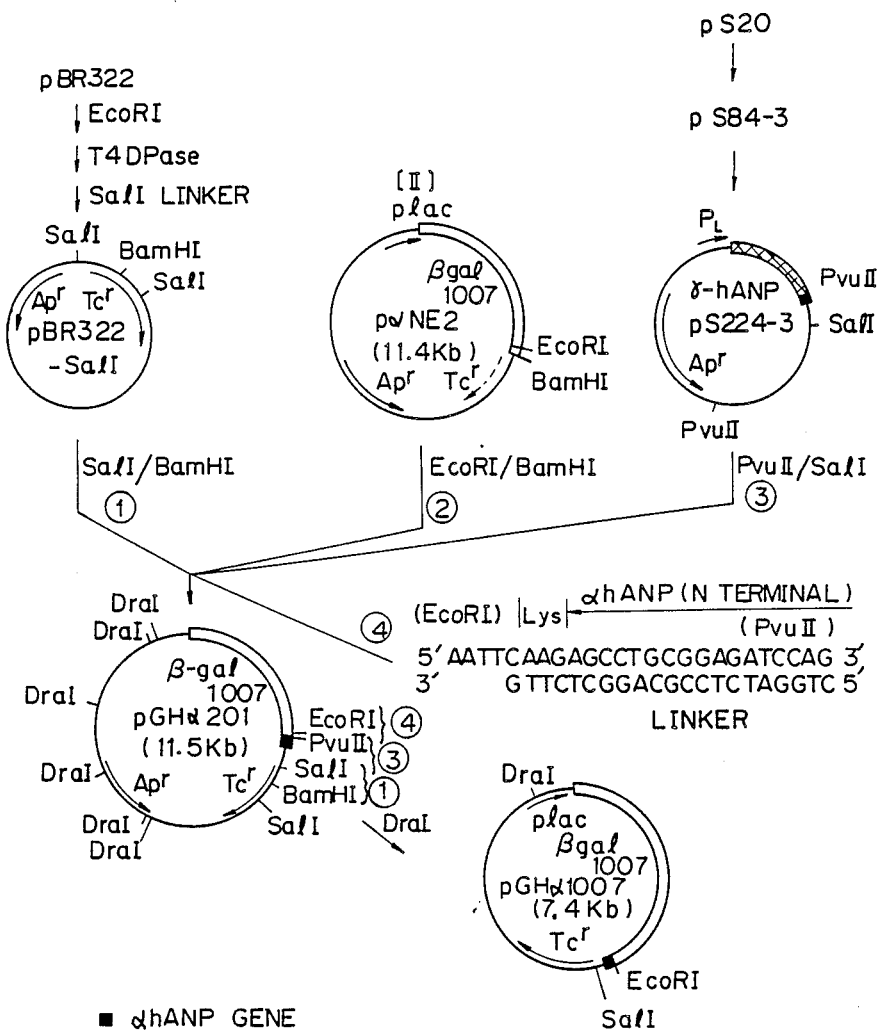
FIG. 11 represents a process for the construction of an expression plasmid pGHα1007 for a fusion protein βgalαhANP.

Reference Example 1. Construction of Expression Plasmid pGHα1007 (FIG. 11)

A. Construction of pBR322-SalI

Five μg of plasmid pBR322 was digested completely with 16 units of EcoRI in 50 μl of HindIII buffer comprising 50 mM Tris-HCl (pH 8.0), 50 mM NaCl, 10 mM MgCl$_2$ at 37° C. for 60 minutes, and the digested DNA was recovered by ethanol precipitation. Next, EcoRI ends of the DNA were converted to blunt ends with 2 μl of 25 mM dNTPs (dATP, dGTP, dCTP and dTPP) using 4 units of T4 DNA polymerase in 100 μl of TA buffer comprising 33 mM Tris-acetate (pH 7.9), 66 mM CH$_3$COONa, 10 mM (CH$_3$COO)$_2$Mg and 0.5 mM dithiothreitol. Next, the DNA was recovered by ethanol precipitation, the DNA was incubated in 20 μl of a ligation mixture comprising 20 mM Tris-HCl (pH 7.4), 10 mM MgCl₂, 10 mM dithiothreitol and 1 mM ATP supplemented with 0.5 μg of the following SalI linker

```
5'-GGGTCGACCC-3'
3'-CCCAGCTGGG-5'
``` with 1 unit of T4 DNA ligase at 15° C. for 18 hours.

The reaction mixture was used to transform *E. coli* W3110, and a clone exhibiting ampicillin and tetracycline resistance (Ap$^r$, Tc$^r$) was obtained, a plasmid was isolated from the clone, and the plasmid was analyzed by restriction enzyme cleavage to confirm conversion of EcoRI site to SalI site. The plasmid was designated as pBR322-SalI.

B. Construction of pGHα201

Five μg of the plasmid pBR322-SalI was partially digested with 8 units of SalI in 50 μl of SalI buffer comprising 6 mM Tris-HCl (pH 7.9), 150 mM NaCl and 6 mM MgCl₂ at 37° C. for 60 minutes, and then digested completely with 24 units of BamHI. The reaction mixture was subjected to agarose gel electrophoresis to recover the second large DNA fragment containing a promoter region of tetracycline resistance gene (No. 1 fragment in FIG. 11).

On the other hand, 5 μg of plasmid paNE2 was digested completely with 24 units of BamHI and 24 units of EcoRI in 100 μl of SalI buffer at 37° C. for 60 minutes, and the reaction mixture was subjected to agarose gel electrophoresis to recover the largest DNA fragment containing β-gal 1007 gene expressed under the lac promotor and ampicillin resistance gene (No. 2 fragment in FIG. 11). The plasmid paNE2 was described in detail in Japanese Unexamined Patent Publication No. 58-63395, and *E. coli* WA 802/paNE2 was designated as SBM 102, and deposited with the FRI as FERM P-6031 on June 19, 1981.

Moreover, 5 μg of plasmid pS224-3 containing γ-hANP gene the 3'-terminal part of which corresponds to an α-hANP gene, described in Japanese Unexamined Patent Publication No. 60-262592, European Patent Publication No. 0164273, was digested completely with 24 units of PvuII and 80 units of SalI in 100 μl of SalI buffer at 37° C. for 60 minutes. The reaction mixture was then subjected to agarose gel electrophoresis to recover the smallest DNA fragment containing the α-hANP gene lacking the N-terminal portion (No. 3 fragment in FIG. 11).

On the other hand, a DNA fragment of the following structure:

```
EcoRI |Lys|  ⎯⎯→ αhANP (N-terminal) PvuII
5' AATTCAAGAGCCTGCGGAGATCCAG 3'
3'      GTTCTCGGACGCCTCTAGGTC 5'
``` was synthesized. The DNA fragment contains a codon for lysine residue as a linker amino acid and a portion of α-hANP gene which supplements the above-mentioned portion lacking in the No. 3 fragment, and has EcoRI site and PvuII site on both terminals respectively. The DNA fragment is that of No. 4 in FIG. 11.

The above-mentioned four DNA fragments were ligated by the same procedure as described above, and the ligation mixture was used to transform *E. coli* W3110, and clones exhibiting ampicillin and tetracycline resistance were obtained. From the clones plasmids were isolated and analyzed by restriction enzyme cleavage to obtain a desired plasmid pGHα201.

C. Construction of pGHα1007

Five μg of the plasmid pGHα201 was digested completely with 24 units of DraI in 50 μl of SalI buffer at 37° C. for 60 minutes, and the largest DNA fragment was recovered by agarose gel electrophoresis. The DNA fragment was ligated according to the same procedure as described above, and the ligation mixture was used to transform *E. coli* W3110, and ampicillin sensitive and tetracycline resistant clones were obtained. Plasmids from the clones were analyzed by restriction enzyme cleavage to select a desired plasmid pGHα1007.

*E. coli* W3110/pGHα1007 containing the plasmid pGHα1007 was designated as SBM 284 and deposited with the FRI as FERM P-8728 on Apr. 3, 1986, and transferred to deposition under the Budapest treaty as FERM BP-1748 on Feb. 22, 1988.

Figure 12:
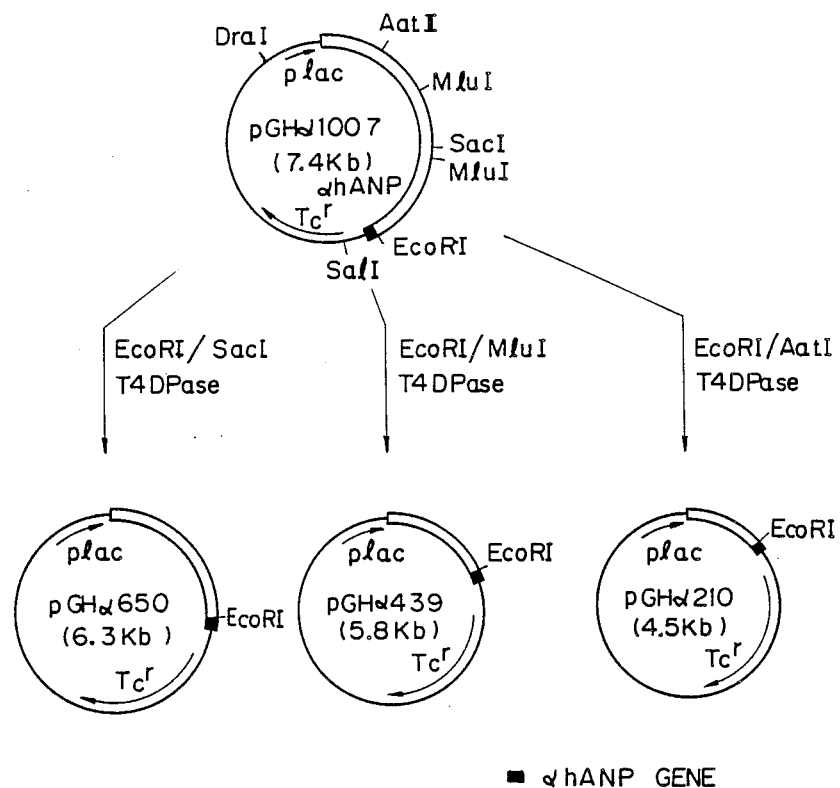
FIG. 12 represents a process for the construction of expression plasmids pGHα650, pGHα439, and pGHα210, each expressing a shortened βgalαhANP fusion protein.

Reference Example 2. Construction of plasmids pGHα650, pGHα439 and pGHα210 (Decrease of size of βgal gene) (FIG. 12)

Five μg of the plasmid pGHα1007 was digested completely with 8 units of EcoRI and 24 units of SacI in 50 μl of TA buffer at 37° C. for 60 minutes. The reaction mixture was subjected to agarose gel electrophoresis to recover the largest DNA fragment. The EcoRI and SacI ends of the DNA fragment were converted to blunt ends according to the same procedure as described above, and the DNA fragment was self-ligated. The ligation mixture was then used to transform *E. coli* W3110 to obtain tetracycline resistant clones. Plasmids were isolated from the clones according to a conventional process by restriction enzyme cleavage to obtain a desired plasmid pGHα650.

Plasmid pGHα439 was constructed according to the same procedure as described above for the construction of plasmid pGHα650 except that HindIII buffer was used in place of the TA buffer, and 24 units of MluI was used in place of SacI. Moreover, plasmid pGHα210 was constructed according to the same procedure as described above for the construction of pGHα650 except that HindIII buffer was used in place of TA buffer, and 24 units of AatII was used in place of SacI.

The plasmid pGHα650 contains DNA fragment coding for a fusion protein designated as βgal 650αhANP wherein the C-terminal of a polypeptide corresponding to 650 amino acid residues of an N-terminal of a βgal protein as partner protein was linked with an N-terminal of α-hANP as the target peptide via two additional amino acid residues Glu-Phe and a linker amino acid lysine. The plasmid pGHα439 has a similar structure to that of pGHα650, except that pGHα439 contains a DNA fragment coding for a fusion protein βgal4-39αhANP wherein the partner protein corresponds to the N-terminal of a β-gal protein consisting of 439 amino acid residues. The plasmid pGHα210 has a similar structure to that of pGHα650 except that pGHα210 contains DNA fragment coding for a fusion protein βgal210αhANP wherein the partner protein corresponds to the N-terminal of a β-gal protein consisting of 210 amino acid residues.

Figure 13:
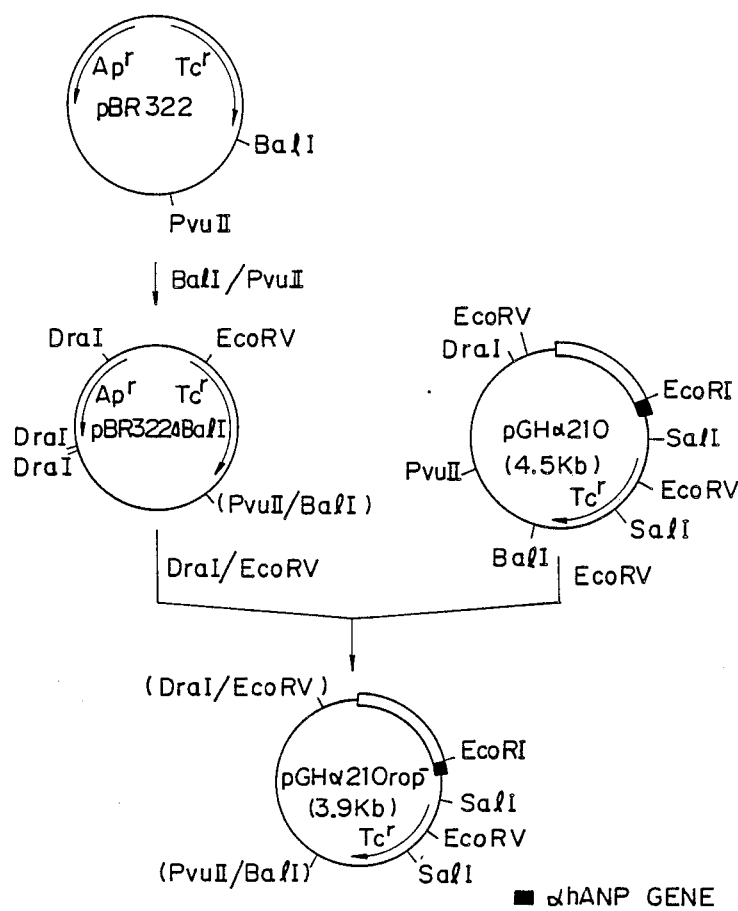
FIG. 13 represents a process for the construction of a plasmid pGHα210rop⁻.

Reference Example 3. Construction of pGHα210rop⁻ (FIG. 13)

A. Construction of pBR322ΔBalI

Five μg of pBR322 was digested completely with 10 units of BalI in 50 μl of BalI buffer comprising 10 mM Tris-HCl (pH 7.6) and 12 mM MgCl$_2$ at 37° C. for 60 minutes, and the digested DNA was recovered by ethanol precipitation. Next, the recovered DNA was dissolved in 50 μl of SalI buffer, and digested completely with 24 units of PvuII, and the reaction mixture was subjected to agarose gel electrophoresis to recover the largest DNA fragment having blunt ends. The DNA fragment was then self-ligated according to the same procedure as described above, and the reaction mixture was used to transform E. coli W3110. Plasmids were obtained from tetracycline and ampicillin resistant clones, and plasmid lacking the PvuII-BalI DNA fragment of 622 bp designated as pBR322ΔBalI was obtained.

B. Construction of pGHα210rop⁻

Five μg of pBR322ΔBalI was digested completely with 24 units of DraI and 24 units of EcoRV in 50 μl of SalI buffer, at 37° C. for 60 minutes and the largest DNA fragment containing an origin of replication was recovered by agarose gel electrophoresis. On the other hand, 5 μg of the plasmid pGHα210 constructed in Reference Example 2 was digested completely with 24 units of EcoRV at 37° C. for 60 minutes, and the second largest DNA fragment containing gene coding for the fusion protein βgal1210αhANP was recovered by agarose gel electrophoresis. These two DNA fragments were ligated according to the same procedure as described above, and the reaction mixture was used to transform E. coli W3110 to obtain tetracycline resistant clones. Plasmids obtained from the clones were analyzed according to a conventional manner, and a desired clone E. coli W3110/pGHα210rop⁻ was obtained. This plasmid pGHα210rop⁻ lacks a function of a region regulating the replication of plasmid (called "rop").

According to the same procedure as described above, but starting with the plasmid pGHα439, plasmid pGHα439rop⁻ lacking a function of rop was constructed.

After preparing transformants E. coli W3110/pGHα439rop⁻ transformed with pGHα439rop⁻ and E. coli W3110/pGHα210rop⁻ transformed with pGHα210rop⁻, amounts of the production of fusion proteins βgal439αANP and βgal1210αhANP were measured by SDS PAGE, and the result was compared with those obtained for plasmids pGHα439 and pGHα210. As a result, it was found that especially in the case of pGHα210, lack of the rop function greatly increased the production of the fusion protein. Note, although when the production of fusion protein was low, the addition of an inducer IPTG was highly effective, and where the number of copies increased due to the lack of the rop function, the addition of IPTG was less effective.

Reference Example 4
Construction of pP$_L$lacZ'210αhANP

Plasmid pP$_L$lacZ'210αhANP wherein lac promoter in pGHα210 was replaced by a P$_L$ promoter of the λ phage was constructed.

Figure 14:
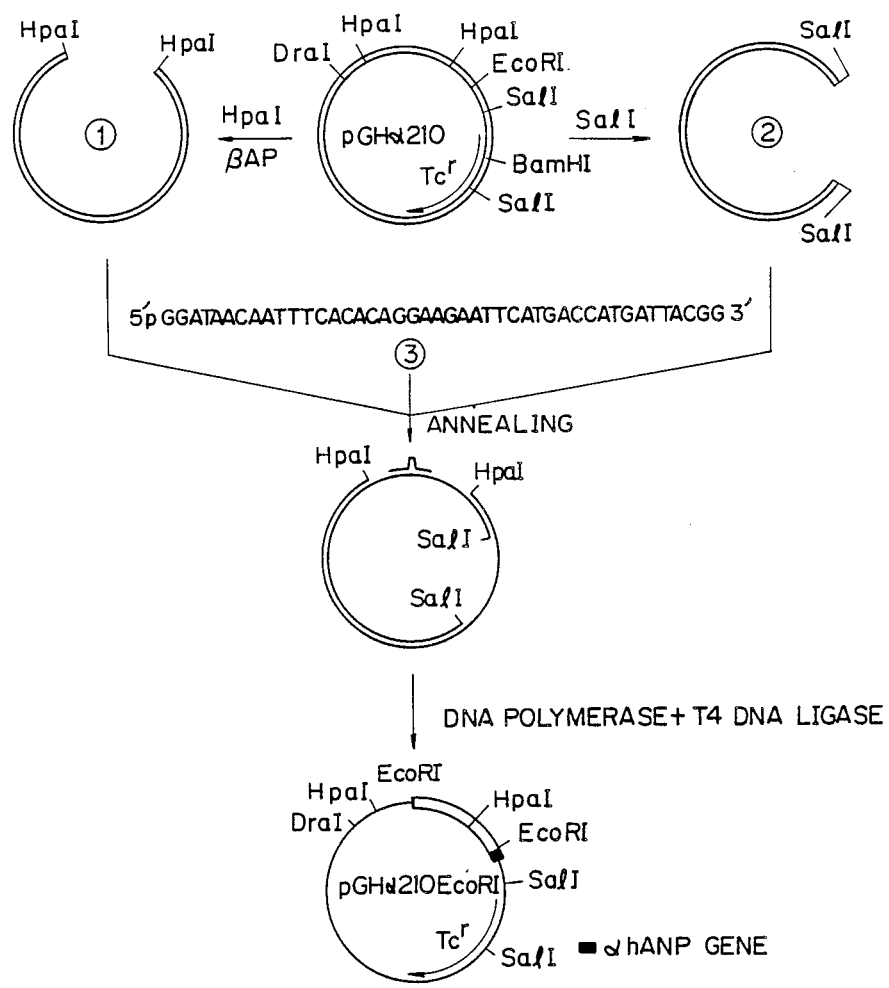
FIG. 14 represents a process for the construction of a plasmid pGHα210EcoRI; and, FIG. 15 represents a process for the construction of a plasmid pPLacZ'210αhANP, which expresses a fusion protein under the control of an P$_L$ promotor of a λ phage.

A. Construction of pGHα210-EcoRI (FIG. 14)

According to the same procedure as described by Morinaga, Y. Biotechnology 2, 636, 1984, an EcoRI site was inserted into pGHα210 immediately upstream of the lacZ' gene to construct a plasmid pGHα210-EcoRI. Namely, 5 μg of pGHα210 was digested to completion with 24 units of HpaI in 50 μl of TA buffer at 37° C. for 60 minutes, and the largest DNA fragment containing α-hANP structural gene and tetracyclic resistance gene (Tc$^r$) (No. 1 fragment in FIG. 14) was electrophoretically separated and recovered. Next, the DNA fragment was treated with alkaline phosphatase in 50 μl of 100 mM Tris-HCl (pH 8.0) buffer to eliminate phosphate at the 5' ends. Next, 5 μg of pGHα210 was digested to completion with 80 units of SalI in 50 μl of SalI buffer at 37° C. for 60 minutes, and the largest DNA fragment lacking a part of the tetracycline resistant gene (No. 2 fragment in FIG. 14) was electrophoretically separated and recovered. On the other hand, a single stranded oligonucleotide having the following sequence:

5'
GGATAACAATTTCACACAGGAAGAATT-
CATGACCATGATTACGG 3' and having EcoRI site and phosphorylated at the 5' end thereof (No. 3 fragment and having EcoRI site in FIG. 14) was chemically synthesized.

Two μg each of the double stranded DNA fragments prepared as above and 1 μg of the above-mentioned chemically synthesized single stranded DNA fragment was mixed in 36 μl of P/L buffer comprising 6 mM Tris-HCl (pH7.5), 50 mM NaCl, 8 mM MgCl$_2$ and 1 mM β-mercaptoethanol, and the mixture was heated to 95° C. to denaturate the double stranded DNA fragment to convert to a single stranded DNA fragment, and gradually cooled to 30° C. over 60 minutes to anneal these DNA fragments. To the reaction mixture were added 1 μl of 25 mM dNTPs and 2 units of Klenow fragment of DNA polymerase, as well as 2 μl of 10 mM ATP and 2 units of T4 DNA ligase, and a reaction was carried out to complete a double stranded circular DNA. The reaction mixture was used to transform E. coli W3110, and tetracycline resistant clones were obtained. Plasmids from the clones were analyzed in a conventional manner to obtain a desired plasmid pGHα210-EcoRI containing a newly added EcoRI immediately upstream of lacZ' gene.

Figure 15:
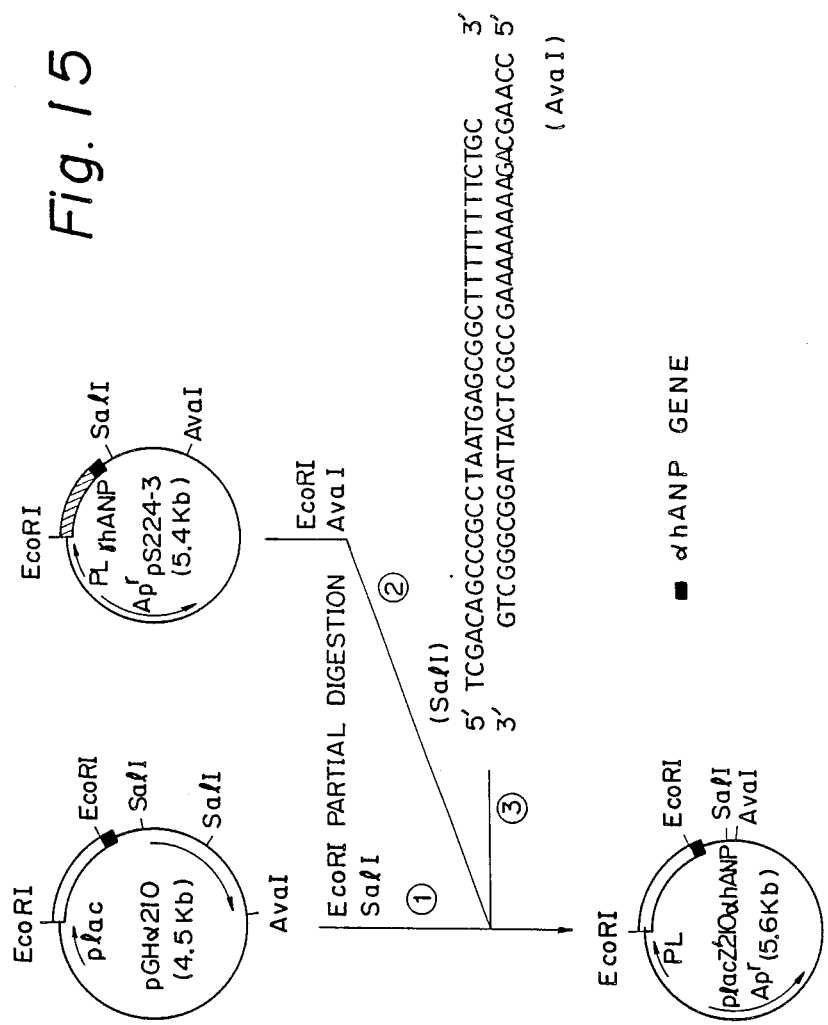

B. Construction of pP$_L$lacZ'210αhANP (FIG. 15)

Five μg of the above-mentioned plasmid pGHα210EcoRI was partially digested with 0.2 units of EcoRI in 50 μl of HindIII buffer at 37° C. for 60 minutes, and the linear DNA fragment was electrophoretically separated and recovered. Next, the recovered DNA fragment was digested completely with 80 units of SalI in 100 μl of SalI buffer at 37° C. for 60 minutes, and the second largest DNA fragment containing a structural gene for βgal210αhANP (No. 1 fragment in FIG. 15) was electrophoretically separated and recovered.

On the other hand, 5 μg of the plasmid pS224-3 described above was digested completely with 16 units of EcoRI and 24 units of AvaI in 50 μl of HindIII buffer at 37° C. for 60 minutes, and the largest DNA fragment containing the P$_L$ promoter of the λ phage and an ampicillin resistance gene (No. 2 fragment in FIG. 15) was electrophoretically separated and recovered.

A double stranded DNA fragment having the following sequence:

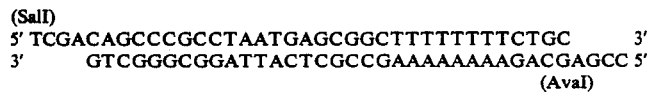

and having a SalI cohesive end and an AvaI cohesive end (No. 3 fragment in FIG. 15) were prepared by chemical synthesis.

These three DNA fragments were ligated according to the same procedure as described above, and the ligation mixture was used to transform E. coli W3110/C₁, and ampicillin and kanamycin resistant clones were obtained. Plasmids from the clones were analyzed in a conventional manner to obtain a desired plasmid pP$_L$lacZ'210αhANP.

Figure 16:
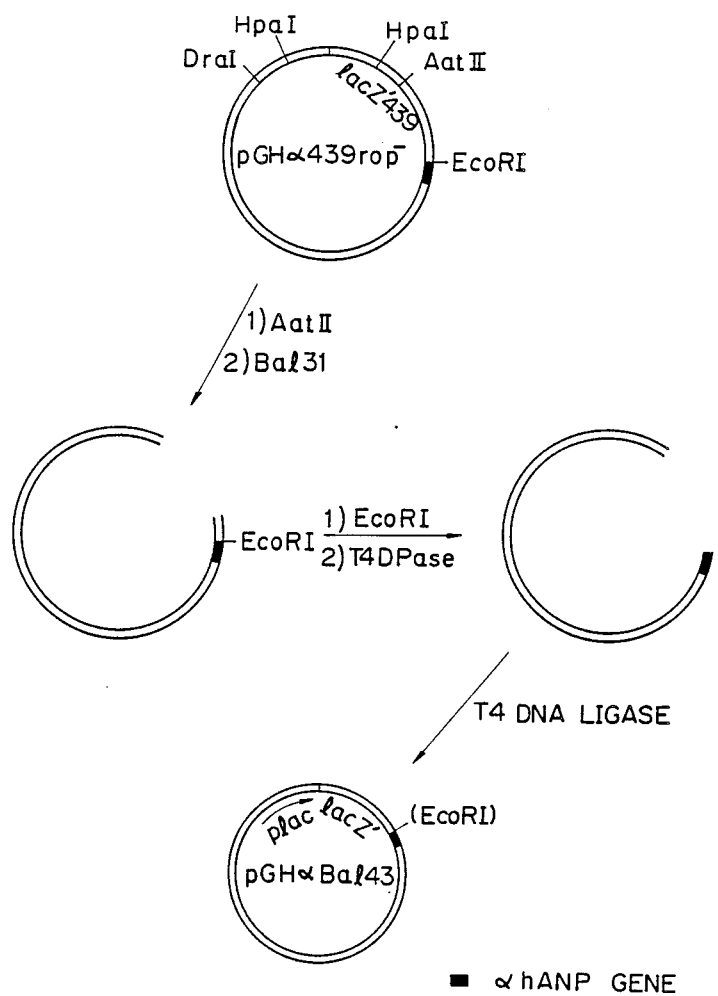
FIG. 16 represents a process for the construction of a plasmid pGHαBal43.

Reference Example 5. Construction of plasmid pGHαBal having shortened β-gal region (FIG. 16)

Ten μg of the plasmid pGHα439rop⁻ constructed in Reference Example 3 was digested completely with 100 units of AatII in 100 μl of HindIII buffer at 37° C. for 60 minutes, and the digested DNA was recovered by ethanol precipitation. Next, the recovered DNA was dissolved in 100 μl of Bal 31 buffer comprising 20 mM Tris-HCl (pH 8.0), 12 mM CaCl₂, 12 mM MgCl₂, 0.2 M NaCl, and 1 mM EDTA, and treated with 10 units of Bal 31. After 5, 10, and 20 minutes, 30 μl of the reaction mixture was sampled and mixed with a same volume of phenol/chloroform 1:1 to terminate the reaction. After eliminating the phenol layer (lower layer), the aqueous layer was extracted with ethyl ether to eliminate the remaining phenol, and DNA was recovered by ethanol precipitation. Next, the DNA fragment from each sample was dissolved in 30 μl of TA buffer, and digested completely with 15 units of EcoRI, and 10 μl of the reaction mixture was subjected to 2% agarose gel electrophoresis. To the remaining 20 μl samples from the 10 minute reaction and 20 minute reaction, which provided a DNA fragment smaller than 400 bp, were added 70 μl of TA buffer, 2 μl of 25 mM dNTPs, 5 μl of 100 mM dithiothreitol and 4 units of T4 DPase, and the reaction was carried out at 37° C. for 30 minutes to convert cohesive ends of the DNA fragment to blunt ends. After collection of each DNA fragment by ethanol precipitation, the DNA fragment was self-ligated with T4 DNA ligase according to the same procedure as described above, and the ligation mixture was used to transform E. coli W3110, and 54 E. coli W3110/pGHα-Bal clones were obtained. Among the plasmids from the 54 clones, the plasmid pGHαBal 43 was used for further experiments.

Reference Example 6. Construction of plasmid pIN5T4 (FIG. 17)

(1) Construction of pIN4GIF54

Figure 17:
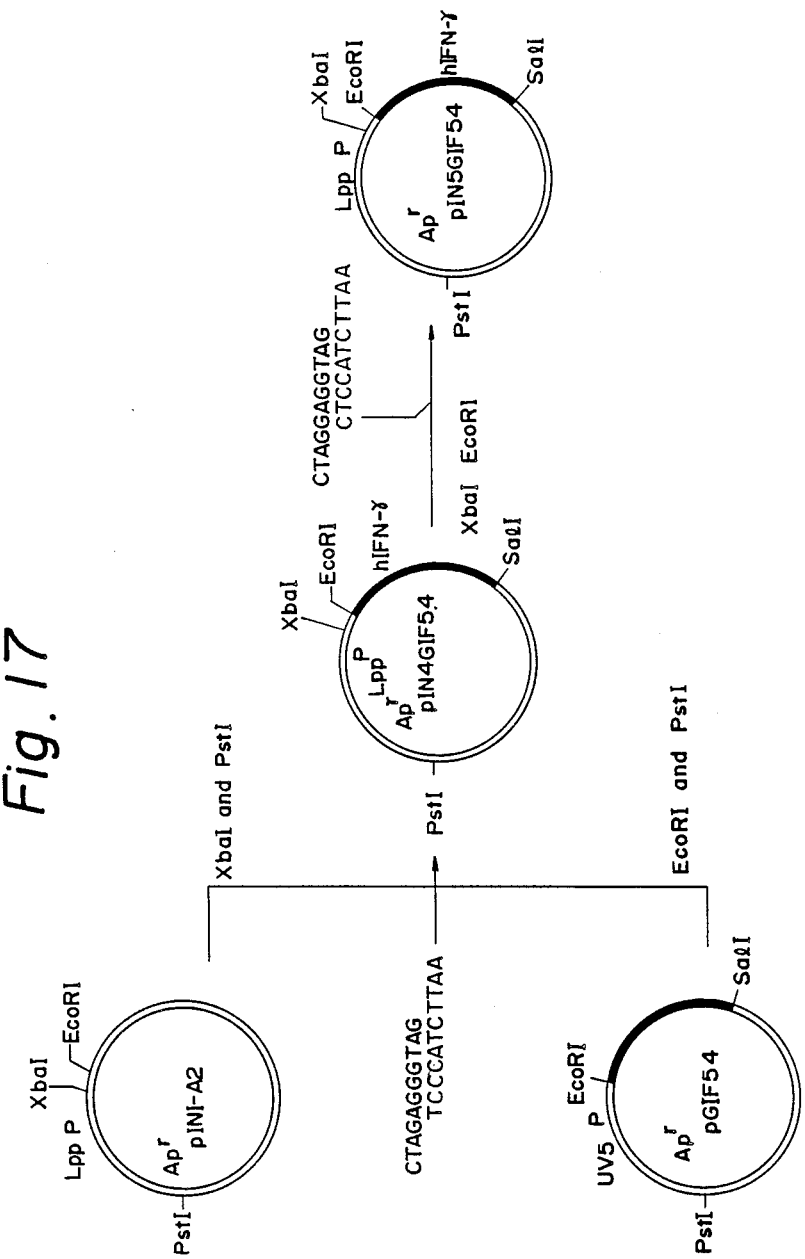
FIG. 17 represents a process for construction of plasmid pIN5GIF54.

Plasmid pIN4GIF54 was constructed, as shown in FIG. 17, from (1) DNA fragment containing the lipoprotein gene promoter region (indicated by lpp in the figure) as obtained by digestion of the plasmid pINIA2 with the restriction enzymes XbaI and PstI, (2) oligonucleotide having XbaI and EcoRI cohesive ends and (3) DNA fragment containing the hINF-γ gene as obtained by digestion of the plasmid pGIF54 with EcoRI and PstI. The procedure followed was as described hereinbelow. The restriction enzymes used were all products of Takara Shuzo KK.

(A) Preparation of XbaI-PstI DNA fragment of pINI-A2

The plasmid pINI-A2 is a gift from Dr. Inoue of New York State University. A host Escherichia coli strain obtained by transformation with said plasmid has been named JA221/pINI-A2 and deposited with the Fermentation Research Institute, 1-3, Higashi 1-chome, Tsukuba-shi, Ibaraki, Japan, under Deposit No. FERM BP-320, on July 18, 1983 under the Budapest treaty.

The pINI-A2 DNA (3 μg) was digested with 15 units each of XbaI and PstI in 150 μl of 1×TA solution (33 mM Tris acetate buffer pH 7.6, 66 mM potassium acetate, 10 mM magnesium acetate and 0.5 mM dithiothreitol) at 37° C. for 60 minutes. The reaction mixture was subjected to 1.0% agarose gel electrophoresis and a gel portion located at the position corresponding to about 980 b.p. (base pairs) was cut out and placed in a dialysis tube, and the XbaI-PstI DNA fragment was eluted by electrophoresis. After removal of ethidium bromide from the eluate by adding an equal amount of phenol thereto, 2.5 volumes of ethanol was added. After standing at −80° C. for 30 minutes, the mixture was centrifuged at 10,000 rpm for 10 minutes, whereby the DNA fragment was obtained as an ethanol precipitate. To this ethanol precipitate was added 10 μl of distilled water for dissolving the DNA fragment.

(B) Preparation of EcoRI-PstI DNA fragment of pGIF54

Figure 6:
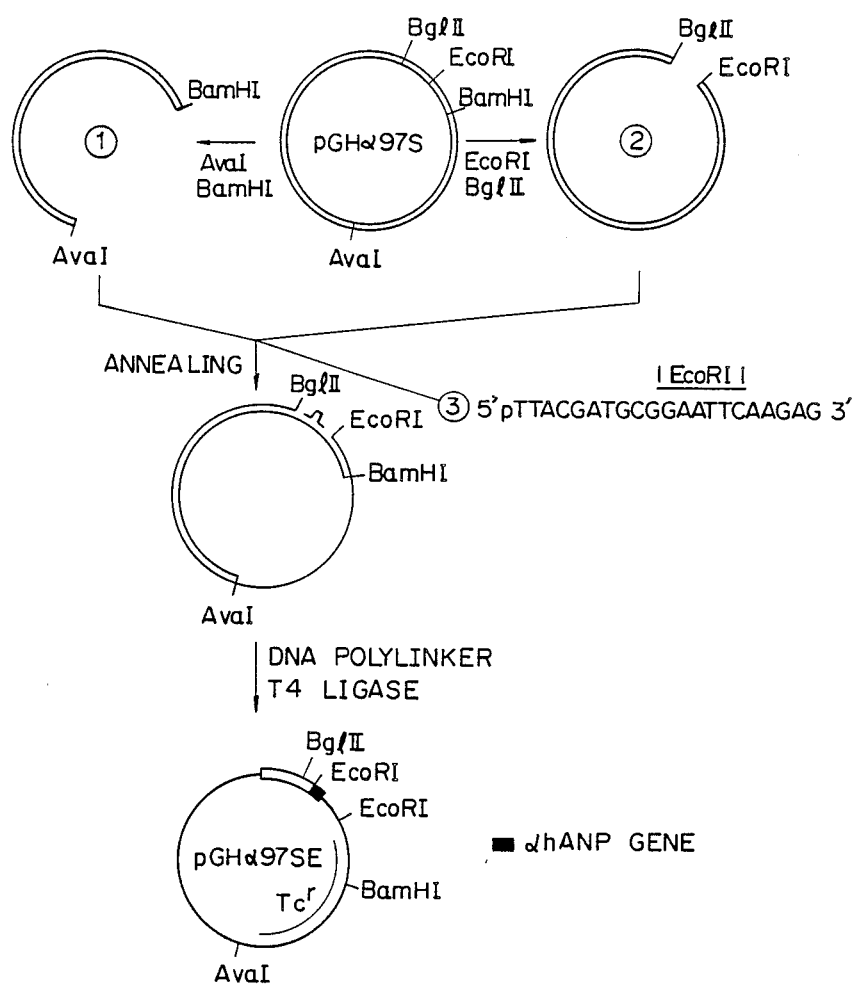
FIG. 6 represents a process for the construction of an expression plasmid pGHα97SE for βgal 97(Ser)αhANP, wherein a junction site between βgal 97(Ser) and α-hANP is converted to Glu-Phe-Lys.

Plasmid pGIF54 is essentially the same plasmid as pGIF4 disclosed in Japanese Patent Application No. 86,180/1982. An Escherichia coli transformant, WA802/pGIF4, obtained by transformation with said plasmid containing the chemically synthesized gene coding for the amino acid sequence of hIFN-γ as shown in FIG. 6 has been named SBMG105 and deposited with the Fermentation Research Institute, the Agency of Industrial Science and Technology as FERM P-6522 on May 6, 1982, and transferred to deposition under the Budapest treaty, as FERM BP-282, on May 2, 1983.

The pGIF54 DNA (3 μg) was digested with 15 units each of EcoRI and PstI in 30 μl of 1×TA solution at 37° C. for 60 minutes, followed by 0.7% agarose gel electrophoresis, whereby an EcoRI-PstI DNA fragment of about 3.4 Kb was eluted from the gel. The eluate was subjected to phenol treatment and ethanol precipitation in the same manner as above. To the ethanol precipitate, 10 μl of distilled water was added for dissolution of the DNA fragment.

(C) Preparation of oligonucleotide having XbaI and EcoRI cohesive ends

For the expression of complete hINF-γ protein, an oligonucleotide having the Shine-Dalgarno (SD) sequence downstream from the XbaI cleavage site of pINIA2 and further having an EcoRI cohesive end, namely the oligonucleotide

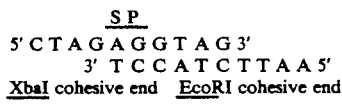

```
5' C T A G A G G T A G 3'
3'     T C C A T C T T A A 5'
XbaI cohesive end    EcoRI cohesive end
``` was synthesized by the solid phase method. The synthetic procedure has been disclosed in detail in Japanese Patent Application No. 86,180/1982.

The above oligonucleotide (100 picomoles) was phosphorylated at the 5'-OH in 30 μl of a kinase reaction solution (50 mM Tris hydrochloride buffer, pH 8.0, 10 mM MgCl₂, 10 mM dithiothreitol), with 2 units of T4 polynucleotide kinase (Takara Shuzo KK) added, at 37° C. for 60 minutes.

(D) Construction of pIN4GIF54

The plasmid pIN4GIF54 was constructed by ligation of the three DNA fragments prepared above in accordance with the following procedure. Thus, to a mixture of 5 μl of a solution of the XbaI-PstI DNA fragment of pINIA2 (solution of the ethanol precipitate in 10 μl of distilled water), 5 μl of a solution of the EcoRI-PstI DNA fragment of pGIF54 (solution of the ethanol precipitate in 10 μl of distilled water) and 3 μl of a solution of the phosphorylated oligonucleotide (10 picomoles), there were added 2 μl of a ligation reaction medium 10-fold higher in concentration (20 mM Tris hydrochloride buffer, pH 7.6, 10 mM MgCl₂), 2 μl of 4 mM ATP and 1 μl of T4 DNA ligase (Boehringer Mannheim) (5 units), and the ligation was carried out at 16° C. overnight.

(2) Transformation of Escherichia coli

(A) Transformation of Escherichia coli WA802

*Escherichia coli* WA802 was cultured in 2.0 ml of L-broth at 37° C. overnight, 0.3 ml of the culture broth was added to 30 ml of L-broth, and the culture was shaken at 37° C. for 2 hours, followed by centrifugation at 3,000 rpm for 10 minutes. To the thus-obtained cells was added 10 ml of 50 mM CaCl₂ for suspending the cells, and centrifugation was conducted at 3,000 rpm for 10 minutes. To the thus-obtained cells was added 1.0 ml of 50 mM CaCl₂ solution, and the mixture was allowed to stand in an ice bath for 60 minutes. To 0.2 ml of this suspension of Ca⁺⁺-treated cells was added 10 μl of the ligation reaction mixture obtained in Example I-D (containing the above-mentioned three DNA fragments ligated), the mixture was allowed to stand in an ice bath for 60 minutes, than 2 ml of L-broth was added and incubation was conducted at 37° C. for 60 minutes. The culture broth was used for plating on nutrient agar medium (BBL) containing 40 μg/ml of ampicillin. After incubation at 37° C. overnight, ampicillin-resistant transformants were selected. One of the transformants obtained was used for plasmid DNA separation therefrom by the conventional method (cleared lysate method). The base sequence of the DNA at and around the XbaI-EcoRI region inserted was determined by the Maxam-Gilbert method (Methods in Enzymology, 65: 499-560, 1980) and it was confirmed that the DNA had the desired DNA base sequence. This plasmid was named pIN4GIF54 and the transformant *Escherichia coli* strain carrying the same was named WA802/pIN4-GIF54.

(3) Construction of pIN5GIF54 plasmid (FIG. 17)

(A) Preparation of oligonucleotide having XbaI and EcoRI cohesive ends

The oligonucleotide having the SD sequence AGGAGGT and XbaI and EcoRI cohesive ends at the 5'-ends, namely

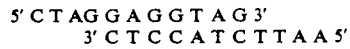

```
5' C T A G G A G G T A G 3'
3'     C T C C A T C T T A A 5'
``` was synthesized by the solid phase method mentioned above (cf. Japanese Patent Application No. 86,180/1982). The above oligonucleotide (100 picomoles) was phosphorylated at the 5'—OH, at 37° C. for 60 minutes, in 50 μl of the kinase reaction solution with 2 units of T4 polynucleotide kinase (Takara Shuzo) added, as mentioned above.

(B) Preparation of XbaI-EcoRI DNA fragment of pIN4GIF54 pIN4GIF54 (2.5 μg) was digested with 5 units each of XbaI and EcoRI in 30 μl of 1×TA solution at 37° C. for 60 minutes for cleaving the DNA. After cleavage, 0.7% agarose gel electrophoresis was carried out and an XbaI-EcoRI DNA fragment of about 4.3 Kb (SD sequence-free longer fragment) was eluted from the gel by electrophoresis as mentioned above. The eluate was subjected to phenol treatment and ethanol precipitation as mentioned above and, to the ethanol precipitate, 10 μl of distilled water was added for dissolution of the DNA fragment.

(C) Construction of pIN5GIF54

The plasmid pIN5GIF54 was constructed by ligating the above two DNA fragments in the following manner. Thus, to 5 μl a solution of the phosphorylated oligonucleotide (10 picomoles), there were added 3 μl of the ligation reaction solution 10-fold in concentration (mentioned hereinbefore), 10 μl of 100 mM DTT and 4 mM ATP in distilled water, and 1 μl (5 units) of T4 DNA ligase (Boehringer Mannheim). The mixture was incubated at 16° C. overnight.

(4) Transformation of *Escherichia coli*

(A) Transformation of *Escherichia coli* WA802

Figure 3:
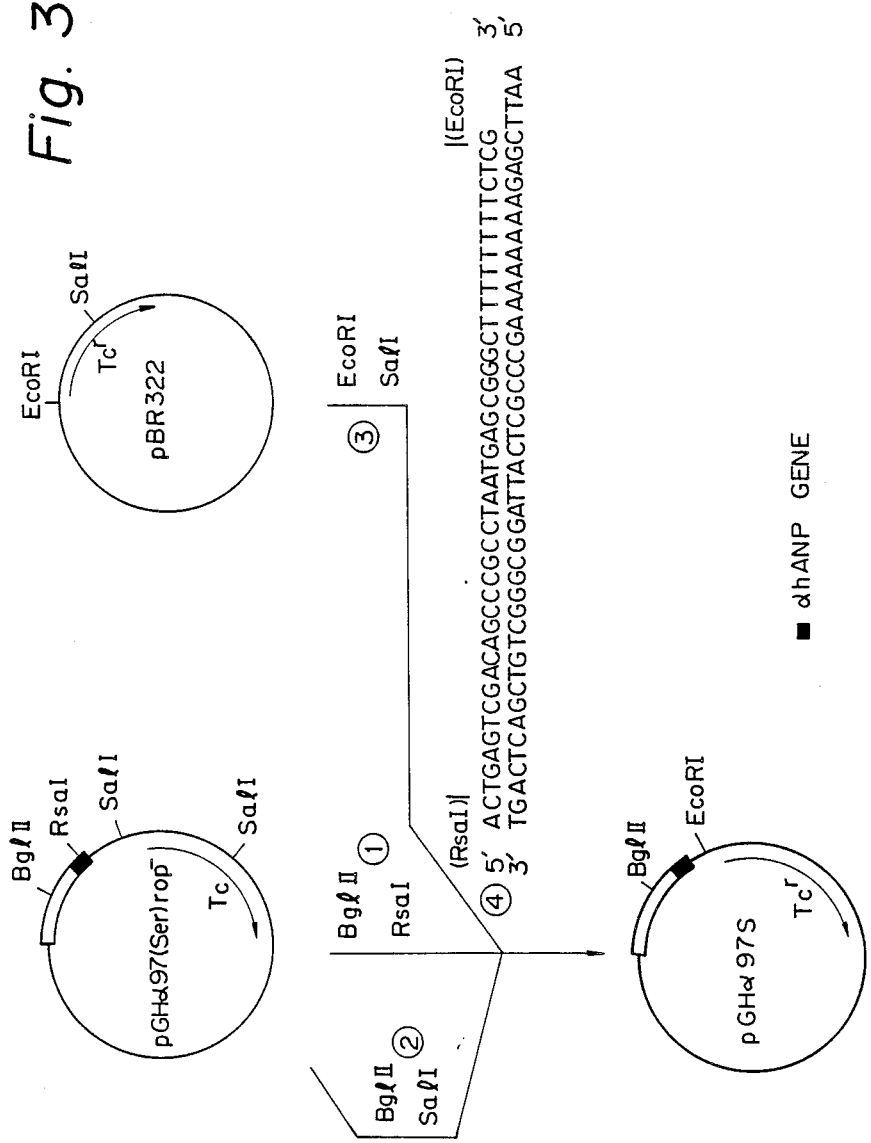
FIG. 3 represents a process for the construction of an expression plasmid pGHα97S for βgalα97(Ser)αhANP, which plasmid is a derivative of the plasmid pGHα97-(Ser)rop⁻ wherein an attenuator terminator of tryptophan operon (trp a) is inserted immediately downstream of α-hANP structural gene in pGHα97(Ser)rop⁻ and the 3'-non-coding region of α-hANP cDNA is eliminated.
Figure 5:
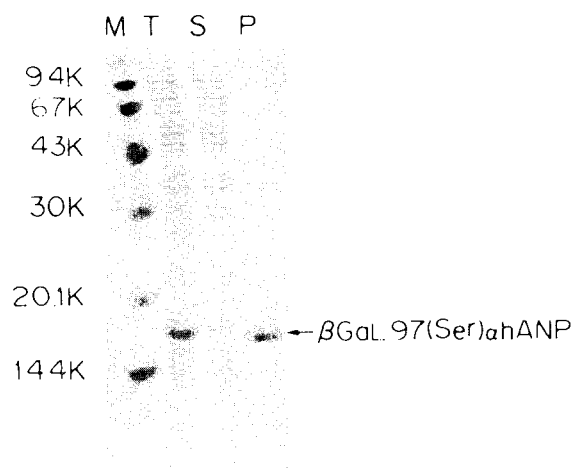
FIG. 5 shows a result of the SDS-PAGE of expression products from *E. coli* W3110/pGHα97S, wherein M represents the molecular weight standard, T represents expression products in a cultured cell disruptant, S represents products in a supernatant from the cell disruptant, and P represents products in a precipitate from the cell disruptant.

In the same manner as above (Example II-A), cells of *Escherichia coli* WA802 as grown in L-broth were treated with CaCl₂, and 0.2 ml of cell suspension was mixed with the ligation reaction mixture obtained in Example IV-C for effecting transformation of *Escherichia coli* WA802. Transformant selection was conducted using a nutrient agar medium (BBL) containing 40 μg/ml of ampicillin. Using one of the transformants thus obtained, plasmid separation was performed by the conventional method (cf. Example II-A), and the DNA base sequence at and around the insert region, namely XbaI-EcoRI region, was analyzed. As shown in FIG. 5, pIN5GIF54 must be free of the XbaI cleavage site originally present in pIN4GIF54 (FIG. 3). Therefore, the plasmid separated was treated with XbaI, followed by 0.7% agarose gel electrophoresis and determination, for the plasmid DNA remaining uncleaved with XbaI, of the DNA sequence at and around the oligonucleotide fragment insert by the Maxam-Gilbert method. The results obtained confirmed the presence of the intended DNA base sequence. This plasmid was named pIN5-

GIF54, and the WA802 strain transformed therewith was named WA802/pIN5GIF54.

Figure 18:
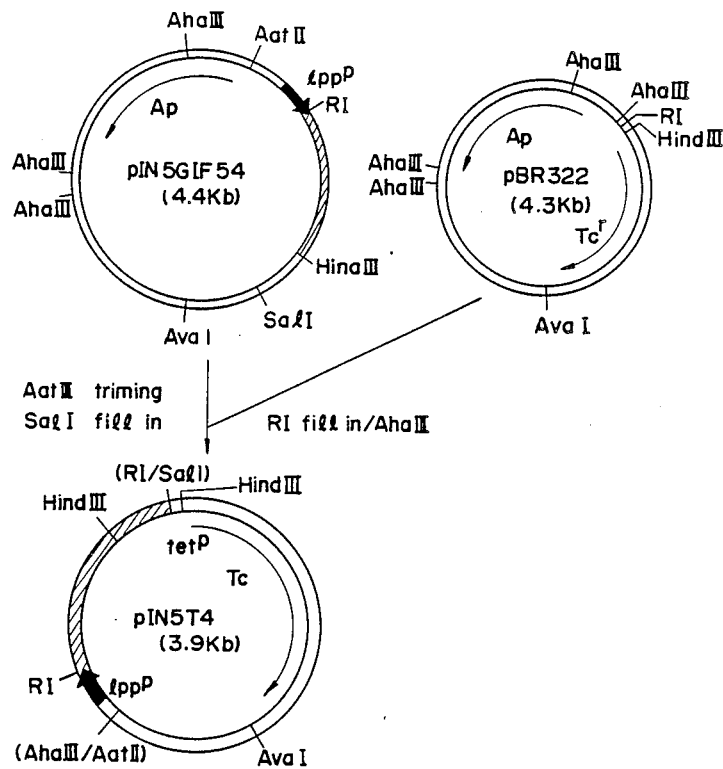
FIG. 18 represents a process for construction of plasmid pIN5T4.

(5) Preparation of pIN5T4 (FIG. 18)

A portion (5 μg) of pIN5GIF54 was completely digested with 20 units of AatII and 20 units of SalI. The cohesive AatII end (3' terminus) and SalI end (5' terminus) were made blunt using T4 DNA polymerase and 4dNTP (including dATP, dGTP, dCTP and dTTP); the AatII end was subjected to trimming whereas the SalI end was subjected to filling-in. The digested plasmid was separated by agarose gel electrophoresis and a DNA fragment (ca. 750 bp) containing the lipoprotein promoter (lppP) and GIF gene was electro-eluted from the gel by electrophoresis. DNA recovery was subsequently made by precipitation with ethanol.

A portion (5 μg) of pBR322 was completely digested with 20 units of EcoRI and the resulting sticky end was made blunt by the filling-in technique described above. The plasmid was then digested completely with 20 units of AhaIII. The digested plasmid was separated by agarose electrophoresis and a DNA fragment (ca. 3.3 kd) containing the DNA replication initiation origin and tetracycline-resistance gene was obtained by the method described above.

The two DNA fragments were mixed, and the mixture was subjected to ligation at 15° C. for 18 hours using T4 DNA ligase (1 unit) in a ligation solution (20 μl) composed of 20 mM tris-HCl (pH 7.4), 10 mM MgCl$_2$, 10 mM DTT (dithiothreitol), and 1 mM ATP. After treatment with 0.3 mL CaCl$_2$, E. coli W3110 was transformed by addition of 10 μl of the ligation solution. Tetracycline resistant clones of the transformants were analyzed routinely to obtain W3110 clones having pIN5T4.

Example 1. Increase of recovery of α-hANP by hydrolysis of βgal210αhANP under DTT reduction

A. Recovery of α-hANP from βgal210αhANP by hydrolysis with API

As described in Reference Example 2, βgal210αhANP is a fusion protein comprising α-hANP and a polypeptide having 210 amino acid residues of β-galactosidase.

E. coli W3110/pGHα210rop⁻ was cultured in a medium containing 0.5% glycerol, 2.4% yeast extract, 1.2% trypton (Trademark for Difco; a product prepared by the partial hydrolysis of casein using typsin) and 100 mM potassium-phosphate (pH 7.5), and supplemented with tetracycline at 37 for 14 hours. Next, the bacterial cells were harvested and suspended in 10 mM Tris-HCl buffer (pH 9.3), and disrupted by ultrasonication. The disrupted product was centrifuged at 10,000 g for one minute to obtain a precipitate. The precipitate was washed with the same buffer, and solubilized in a same buffer containing 5M urea. An aliquot of the mixture was subjected to SDS polyacrylamide gel electrophoresis (SDS-PAGE) to determine an amount of fusion protein produced. The remaining reaction mixture was hydrolyzed with API (Achromobacter protease I; Wako Junyaku, Japan) and an aliquot of the reaction mixture was subjected to SDS-PAGE to confirm completion of the hydrolysis. The reaction mixture was then analyzed by HPLC using YMC-A-302ODS column to determine the amount of liberated α-hANP. The amount of β-hANP estimated from HPLC was about one fourth of the amount estimated from SDS-PAGE, suggesting that α-hANP bonded to a partner protein βgal 210 in any manner cannot be liberated. As the reason for this phenomenon, it may be suggested that at least one of three cysteine residues present with βgal 210 protein consisting of 210 amino acid residues derived from β-galactosidase and at least one of two cysteine residues present in α-hANP form disulfide bond(s), and therefore, α-hANP molecule cut off from βgal 210 molecule at a peptide bond adjacent to a linker amino acid is bonded to the βgal 210 molecule via the disulfide bond(s).

To confirm this speculation, the following experiments were carried out.

B. Increase of recovery of α-hANP from hydrolyzed βgal210αhANP by DTT reduction To determine the involvement of disulfide bonds, βgal210αhANP preparation hydrolyzed with API was reduced with DTT and amount of α-hANP was measured by HPLC. As a result, as shown in Table 1, the amount of liberated α-hANP was increased four times in comparison with the amount thereof before the reduction with DTT. The amount of liberated α-hANP after the DTT reduction is approximately the same as an amount approximated from the result of SDS-PAGE. From the above-mentioned result, it is suggested that the low recovery of α-hANP from βgal210αhANP after API hydrolysis is due to the presence of the disulfide bonds between βgal 210 molecule and α-hANP molecule.

Example 2. Conversion of cysteine residue to serine residue in βgal 210

To confirm the involvement of disulfide bonds in the low recovery of α-hANP from βgal210αhANP after API hydrolysis, and to improve native βgal 210 as a partner in a fusion protein, all cysteine residues present in native βgal 210 were replaced by serine residues. The modified βgal 210 protein wherein all cysteine residues are replaced by serine residues is designated as βgal210(Ser); and a fusion protein comprising α-hANP and the βgal210(Ser) is designated as βgal210(Ser)αhANP.

A. Construction of plasmid pGHα210(Ser)rop⁻ (FIG. 1)

βgal 210 protein contains three cysteine residues at the positions 76, 122 and 154 calculated from the N-terminal. Plasmid pGHα210(Ser)rop⁻ containing a gene coding for a fusion protein comprising α-hANP and modified βgal 210 wherein the above-mentioned three cysteine residues are converted to serine residues. The Cys→Ser conversion provides restriction enzyme cleavage sites BglII, BamHI and AvaII.

Three μg of the plasmid pGHα210rop⁻ constructed in Reference Example 3 was digested completely with 20 units of PvuI and 12 units of EcoRI in 50 μl of H buffer comprising 10 mM Tris-HCl (pH 8.0), 7 mM MgCl$_2$ and 100 mM NaCl at 37° C. for 60 minutes, and the largest DNA fragment containing tetracycline gene (No. 1 fragment in FIG. 1) was electrophoretically separated and recovered. In the same manner, 3 μg of pGHα210rop⁻ was digested completely with 20 units of AvaI and 20 units of BamHI in 50 μl of H buffer at 37° C. for 60 minutes, and the largest DNA fragment containing lacZ'210-αhANP gene (No. 2 fragment in FIG. 1) was electrophoretically separated and recovered.

On the other hand, three oligonucleotide primers having the following sequences:

BglII
(3) 5' pCTTGCTGGAGTCAGATCTTCCTGAG 3'
        BamHI (4) 5' pGAATCCGACGGGATCCTACTCGCTCAC 3'
        AvaII (5) 5' pCATCTGTGGTCCAACGGGCG 3' were chemically synthesized. Each oligonucleotide contains a codon for serine in place of a codon for cysteine, and a restriction enzyme cleavage site BglII, BamHI or AvaII, and have been phosphorylated at the 5'-ends thereof.

Two μg each of the above-prepared double stranded DNA fragments and 1 μg each of the three oligonucleotide primers were mixed in 30μl of buffer P/L buffer comprising 6 mM Tris-HCl (pH7.5), 50 mM NaCl, 8 mM MsCl₂ and 1 mM β-mercaptoethanol, and the mixture was heated to 95° C. to denature the double stranded DNA fragments to form single stranded DNA fragment, and gradually cooled to 30° C. for 60 minutes to anneal the DNA fragments. To the reaction mixture were added 1 μg of dNTPs and 2 units of Klenow fragment of DNA polymerase, as well as 2 units of T4 DNA ligase and 2 μl of 10 mM ATP to complete a circular double stranded DNA. The reaction mixture was used to transform E. coli W3110 to obtain tetracycline resistant clones. Plasmids from the clones were analyzed in a conventional manner to obtain a desired plasmid pGHα210(Ser)rop⁻ containing newly introduced restriction sites BglII, BamHI and AvaII.

B. Recovery of α-hANP from βgal210(Ser)αhANP

E. coli W3110/pGHα210(Ser)rop⁻ was cultured in a medium containing 0.5% glycerol, 2.4% yeast extract, 1.2% trypton and 100 mM potassium-phosphate (pH 7.5), and supplemented with tetracycline at 37 for 14 hours. Next, the bacterial cells were harvested and suspended in 10 mM Tris-HCl buffer (pH 9.3), and disrupted by ultrasonication. The disrupted product was centrifuged at 10,000 g for 5 minutes to obtain a precipitate. The precipitate was washed with the same buffer, and solubilized in a same buffer containing 5 M urea. An aliquot of the mixture was subjected to SDS-polyacrylamide gel electrophoresis (SDS-PAGE) to determine an amount of fusion protein produced. The remaining reaction mixture was hydrolyzed with API (Achromobacter protease I; Wako Junyaku, Japan) and an aliquot of the reaction mixture was subjected to SDS-PAGE to confirm completion of the hydrolysis. The reaction mixture was then analyzed by HPLC using YMC-A-302ODS column to determine the amount of liberated α-hANP. The amount of liberated α-hANP obtained from the result of HPLC was roughly the same as that estimated from a result of SDS-PAGE, and DTT-reduction of API-hydrolyzed sample did not increase the amount of α-hANP liberated, as shown in Table 1. This result demonstrates that lower recovery of α-hANP from βgal210αhANP is due to the presence of cysteine residues in βgal 210 protein. Moreover the above-mentioned result shows that α-hANP can be easily isolated from the fusion protein βgal210(Ser)αhANP without DTT-reduction and, therefore, without subsequent oxidation.

TABLE 1

| Fusion Protein | Amount of α-hANP liberated | |
|---|---|---|
| | −DTT | +DTT |
| βgal210αhANP | 6.7 mg (0.25) | 27.3 mg (1.00) |
| βgal210(Ser)αhANP | 24.2 mg (0.97) | 25.0 mg (1.00) |

A process for the production of α-hANP through a fusion protein βgal210(Ser)αhANP has advantages, in addition to that (1) α-hANP can be produced in a large amount and (2) since expressed fusion protein is transferred to a precipitate while impurity proteins remain in a supernatant, the fusion protein is easily purified, as in use of βgal210αhANP, that (3) since βgal210(Ser) does not contain cysteine residue and, therefore, a disulfide bond is not formed between α-hANP and βgal210(Ser), α-hANP can be almost completely recovered from API-hydrolyzed fusion protein without DTT-reduction and subsequent oxidation. In industrial production of α-hANP, however, there are some problems. Namely, (a) since the fusion protein βgal210(Ser)αhANP has a low solubility in an urea aqueous solution, a low concentration of the fusion protein, i.e., high dilution of a reaction mixture is required in the API-hydrolysis process, and (b) since the efficiency of API-hydrolysis on βgal210(Ser)αhANP is rather low, a large amount of API enzyme per substrate and long reaction time is necessary, with a possibility of an undesirable modification of the target product α-hANP.

Taking into account the above-mentioned situation, to resolve the problems (a) and (b) while maintaining the advantages (1), (2), and (3) the present inventors attempted to shorten the size of a partner protein. For this purpose, a plasmid containing a DNA coding for a fusion protein comprising α-hANP and a partner peptide of 97 amino acid derivative corresponding to the N-terminal of a β-galactosidase protein wherein 76th cysteine is replaced by serine was constructed. The peptide consisting of 97 amino acid residues of β-galactosidase is designated as βgal 97; and the fusion protein comprising α-hANP and the βgal 97 is designated as βgal97αhANP. Moreover, the peptide consisting of 97 amino acid residues of β-galactosidase wherein 76th cysteine is replaced by serine is designated βgal97(Ser); and the fusion protein comprising α-hANP and the βgal97(Ser) is designated βgal97(Ser)αhANP.

Example 3. Construction of plasmid pGHα97S

A. Construction of plasmid pGH97(Ser)rop⁻

Plasmid pGHα97(Ser)rop⁻ containing a gene for βgal97(Ser)αhANP wherein 76th amino acid cysteine has been replaced by serine in the fusion protein βgal9-7αhANP was constructed.

Figure 2:
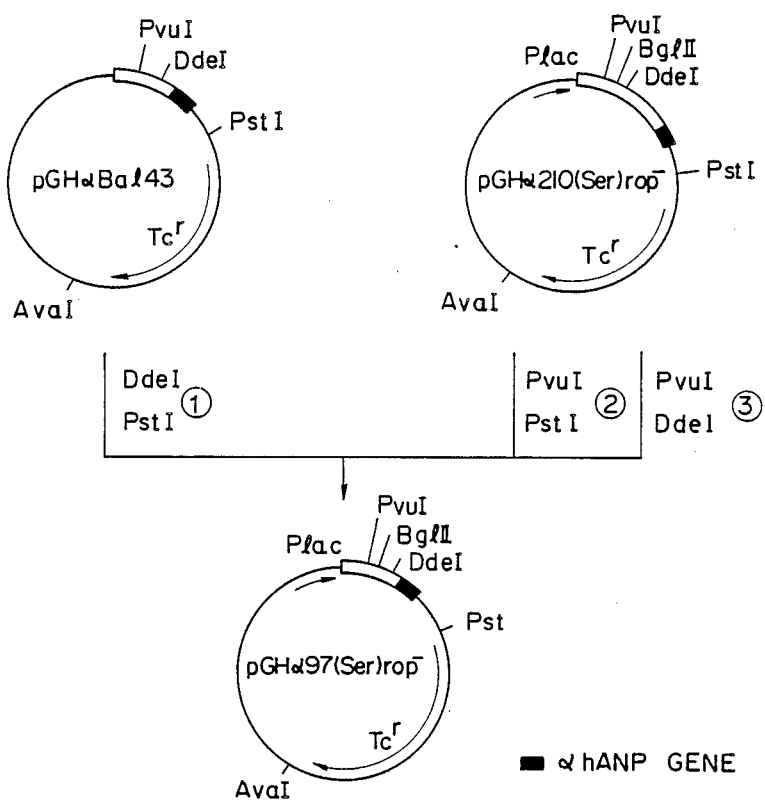
FIG. 2 represents a process for the construction of an expression plasmid pGHα97(Ser)rop⁻ for a fusion protein comprising α-hANP and βgal 97(Ser) as a partner protein. The βgal 97(Ser) is a derivative of a βgal 97 protein wherein cysteine residues of βgal 97 are replaced by serine residues.

Ten μg of the plasmid pGHαBal43 constructed in Reference Example 5 was digested completely with 50 units of PstI and 50 units of DdeI in 70 μl of H buffer at 37° C. for 60 minutes, and the digestion product was subjected to agarose gel electrophoresis to separate and recover a 283 bp DNA fragment containing α-hANP gene (No. 1 fragment in FIG. 2). On the other hand, 3 μg of the plasmid pGHα210(Ser)rop⁻ constructed in Example 1 was digested completely with 20 units of PvuI and 20 units of PstI in 50 μl of H buffer at 37° C. for 60 minutes, and the largest DNA fragment containing tetracycline resistant gene (No. 2 fragment in FIG.

2) was electrophoretically separated and recovered. Moreover, 10 µg of pGHα210(Ser)rop⁻ was digested completely with 50 units of PvuI and 50 units of DdeI in 70 µl of H buffer, and a 101 bp DNA fragment containing a part of lacZ' gene (No. 3 fragment in FIG. 2) was separated and recovered by agarose gel electrophoresis.

These three DNA fragments were ligated in 20 µl of ligation mixture comprising 20 mM Tris-HCl(pH7.4), 10 mM MgCl₂ and 10 mM dithiothreitol using 1 unit of T4 DNA ligase at 15° C. for 18 hours, and the reaction mixture was used to transform E. coli W3110 to obtain tetracycline resistant clones. Plasmids from the clones were analyzed in a conventional manner to select a desired plasmid pGHα97(Ser)rop⁻ containing lacZ' gene coding for fusion protein βgal97(Ser)αhANP wherein 76th cysteine has been replaced by serine.

Escherichia coli SBM288 containing the plasmid pGHα97(Ser)rop⁻ was deposited with the FRI under the Budapest treaty as FERM BP-1253 on Jan. 9, 1987.

B. Construction of pGHα97S

When E. coli W3110/pGHα97(Ser)rop⁻, i.e., E. coli W3110 transformed with plasmid pGHα97(Ser)rop⁻ was cultured in a medium containing 0.5% glycerol, 2.4% yeast extract, 1.2% trypton and 100 mM potassium-H-phosphate (pH 7.5) and supplemented with tetracycline at 37° C. for 14, the productivity of βgal97(Ser)αhANP was lower than that of βgal97αhANP. Therefore, to improve the productivity of βgal97(Ser)αhANP, an attenuator terminator of tryptophan operon (trp a) was inserted immediately downstream of the α-hANP structural gene to construct plasmid pGHα97S.

Ten µg of the plasmid pGHα97(Ser)rop⁻ was digested completely with 50 units of BglII and 50 units of RsaI in 100 µl of H buffer at 37° C. for 60 minutes, and a 154 bp DNA fragment containing C-terminal region of βgal97(Ser) gene and N-terminal region of α-hANP gene (No. 1 fragment in FIG. 3) was electrophoretically separated and recovered. Next, 3 µg of pGHα97(Ser)rop⁻ was digested completely with 20 units of BglII and 40 units of SalI in 50 µl of S buffer comprising 10 mM Tris-HCl (pH 8.0), 150 mM NaCl and 7 mM MgCl₂ at 37° C. for 60 minutes, and the largest DNA fragment containing an origin of replication (No. 2 fragment in FIG. 3) was electrophoretically separated and recovered. Moreover, 3 µg of pBR322 was digested completely with 10 units of EcoRI and 40 units of SalI in 50 µl of S buffer at 37° C. for 60 minutes, and a smaller DNA fragment containing a promoter region of tetracycline resistant gene (No. 3 fragment in FIG. 3) was electrophoretically separated and recovered.

On the other hand, a chemically synthesized double stranded DNA fragment having the following sequence:

```
           (RsaI)                                              (EcoRI)
5' ACTGAGTCGACAGCCCGCCTAATGAGCGGGCTTTTTTTCTCG       3'
3' TGACTCAGCTGTCGGGCGGATTACTCGCCCGAAAAAAAAGAGCTTAA  5'
``` and having RsaI blunt end and EcoRI cohesive end at its ends (No. 4 fragment in FIG. 3) was prepared.

The above-prepared four DNA fragments were ligated by the same procedure as described above, and the ligation mixture was used to transform E. coli W3110. Tetracycline resistant clones were obtained, and plasmids from the clones were analyzed in a conventional manner to obtain the desired plasmid pGHα97S.

C. Production of βgal97(Ser)αhANP

E. coli W3110/pGHα97(Ser)rop⁻, and E. coli W3110/pGHα97S, i.e., E. coli W3110 transformed with pGHα97S were cultured in a medium containing 0.5% glycerol, 2.4% yeast extract, 1.2% trypton, 100 mM potassium-H-phosphate (pH 7.5), supplemented with tetracycline at 37° C. for 14 hours, and amounts of produced βgal97(Ser)αhANP were compared by SDS-PAGE according to the same procedure as described in Example 2. B. for analysis of fusion protein. As seen from FIG. 4, by introducing trp immediately downstream of α-hANP gene the productivity of βgal97(Ser)αhANP remarkably increased. Amount of βgal97(Ser)αhANP produced by E. coli W3100/pGHα97S is approximately the same amount of βgal210(Ser)αhANP produced by E. coli W3110/pGHα210(Ser)rop⁻; this means that the productivity of α-hANP per culture medium in the case of W3110pGHα97S is about two times higher than that in the case of W3110 pGHα210-(Ser)rop⁻. The fusion protein βgal97(Ser)αhANP also, the same as βgal210αhANP andβga210(Ser)αhANP, transferred to a precipitation fraction during centrifugation of the cell disruptant, while E. coli proteins are transferred to a supernatant fraction (see FIG. 5).

As seen from Table 2, although the amount of α-hANP liberated from API-hydrolyzed βgal97αhANP was increased by DTT-reduction as in the case of βgall210αhANP, the amount of αhANP liberated from API-hydrolyzed βgal97(Ser)αhANP was not increased by DTT-hydrolyzed reduction as in the case of βgal210(Ser)αhANP.

TABLE 2

| Fusion Protein | Amount of α-hANP liberated | |
|---|---|---|
| | −DTT | +DTT |
| βgal97αhANP | 7.8 mg (0.31) | 25.0 mg (1.00) |
| βgal97(Ser)αhANP | 24.8 mg (0.80) | 30.9 mg (1.00) |

Moreover, the solubility of the fusion protein βgal97-(Ser)αhANP in a 5 M urea aqueous solution is about ten times higher than that of βgal210(Ser)αhANP. This means, taking into account the fact that the proportion of α-hANP in βgal97(Ser)αhANP is about two times higher than that in βgal210(Ser)αhANP, that concentration of α-hANP in βgal97(Ser)αhANP dissolved in 5 M urea is about 20 times higher than that in the case of βgal210(Ser)αhANP.

The sensitivity of βgal97(Ser)αhANP to API-hydrolysis was about 100 times higher (about 200 times for α-hANP per se.) than that of βgal210(Ser)αhANP.

Accordingly, in the next Example, the reason for the high sensitivity of βgal97(Ser)αhANP to API-hydrolysis was studied.

Example 4. Study of reason of high sensitivity of βgal97(Ser)αhANP to API-hydrolysis In βgal97(Ser)αhANP, βgal97(Ser) is linked with α-hANP via Gln-Phe-Lys wherein Gln is the 98th amino acid in βgal97(Ser)αhANP, and API hydrolyzes a peptide bond at the C-terminal side of Lys. On the other hand, in βgal210(Ser)αhANP, βgal210(Ser) is linked with α-hANP via Glu-Phe-Lys wherein Glu is the 211th amino acid in βgal210(Ser)αhANP. The present invention hypothesized that the reason why βgal97-(Ser)αhANP is more sensitive to API-hydrolysis than βgal210(Ser)αhANP is because although the negative charge on σ carboxyl group of Glu in βgal210(Ser)αhANP interferes with the positive charge on Lys, σ carboxyamide of Gln in βgal97(Ser)αhANP does not have a corresponding negative charge and, therefore, there is no interference with a corresponding positive charge on Lys.

To confirm the hypothesis, plasmid pGHα97SE containing a gene coding for a fusion protein βgalα97(Ser)αhANP wherein 97th amino acid Gln in βgal97(Ser)αhANP has been replaced by Glu (that is, Gln-Phe-Lys at junction part has been converted to Glu-Phe-Lys) was constructed, and the sensitivities of fusion proteins from plasmids pGHα97S and pGHα97SE were compared.

A. Construction of plasmid pGHα97SE

Three μg of the plasmid pGHα97S constructed in Example 3 was digested completely with 20 units of BamHI and 20 units of AvaI in 50 μl of H buffer at 37° C. for 60 minutes, and the largest DNA fragment containing α-hANP gene (No. 1 fragment in FIG. 6) was electrophoretically separated and recovered. Moreover, 3 μg of pGHα97S was digested completely with 20 units of BglII and 20 units of EcoRI in 50 μl of H buffer at 37° C. for 60 minutes, and the largest DNA fragment containing tetracycline resistant gene (No. 2 fragment in FIG. 6) was electrophoretically separated and recovered.

On the other hand, a single stranded oligonucleotide having the following sequence:

|EcoRI|
5' pTTACGATGCGGAATTCAAGAG 3' containing a codon for glutamic acid in place of a codon for glutamine, and phosphorylated at the 5'-end thereof (No. 3 fragment in FIG. 6) was chemically synthesized.

The above-prepared two double stranded DNA fragments and the single stranded origonucleotide were mixed in P/L buffer, and the mixture was heated to 95° C. to denaturate the double stranded DNA fragments to form single stranded DNA fragments, and gradually cooled to 30° C. for 60 minutes to anneal the DNA fragment to double stranded DNA. To the reaction mixture, were added dNTPs and DNA polymerase Klenow fragment, as well as T4 DNA ligase and ATP, and reaction was carried out to form a closed circular. The reaction mixture was used to transform E. coli W3110. Tetracycline resistant clones were obtained, and plasmids from the clones were analyzed in a conventional manner to select a desirable plasmid pGHα97SE containing a gene coding for βgalα97(Ser)EαhANP wherein amino acid residues at junction region Gln-Phe-His has been converted to Glu-Phe-Lys.

B. Comparison of βgal97(Ser)αhANP and βgal97(Ser)EαhANP in API sensitivity

E. coli W3100/pGHα97S and E. coli W3100/pGHα97ES were cultured in a medium containing 0.5% glycerol, 2.4% yeast extract, 1.2% trypton and 100 mM potassium-H-phosphate (pH 7.5) supplemented with tetracycline at 37° C. for 14 hours. The cultured broth was centrifuged to harvest the bacterial cells which were then suspended in 10 mM Tris-HCl (pH 9.3), and disrupted by ultrasonication. The disrupted product was then centrifuged at 10000 g for one minute to obtain a precipitate, which was then washed with the same buffer. The washed precipitate was solubilized in the same buffer containing 5M urea, and the solubilized preparation was divided into four portions. To these preparations, 0, 1, 5, and 25 ng/5 μg αhANP of API were added respectively. Each mixture was incubated at 30° C. for 45 minutes, and analyzed by SDS-PAGE.

Figure 7:
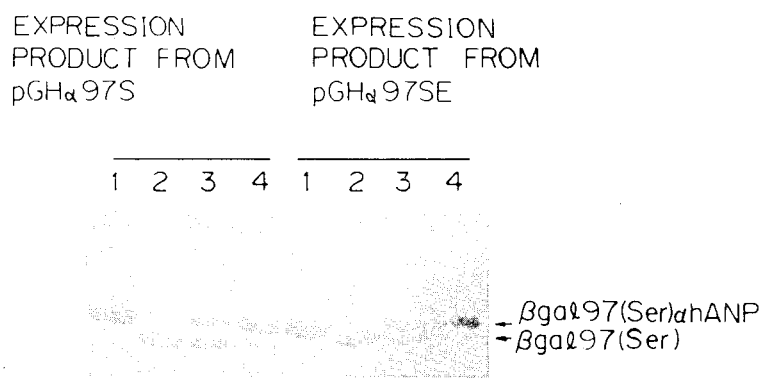
FIG. 7 shows a result of an SDS-PAGE of expression products from the plasmid pGHα97S and pGHα97SE hydrolysed with API. The SDS-PAGE compares the difference in the efficiency of a hydrolysis of the fusion proteins caused by the difference in the junction site of α-hANP with βgal 97(Ser)

As seen from FIG. 7, βgal97(Ser)EαhANP and βgal97(Ser)αhANP did not have different sensitivities to API-hydrolysis. Therefore, the above-mentioned hypothesis was denied. Probably, the high sensitivity of βgal97(Ser)αhANP to API-hydrolysis is due to the structure of βgal97(Ser)αhANP per se.

Example 5. Construction of pP$_L$lacZ'97(Ser)αhANP

Plasmid pP$_L$lacZ'97(Ser)αhANP was constructed by replacing the lac promoter in pGHα97S by a P$_L$ promoter of the λ phage.

Figure 4:
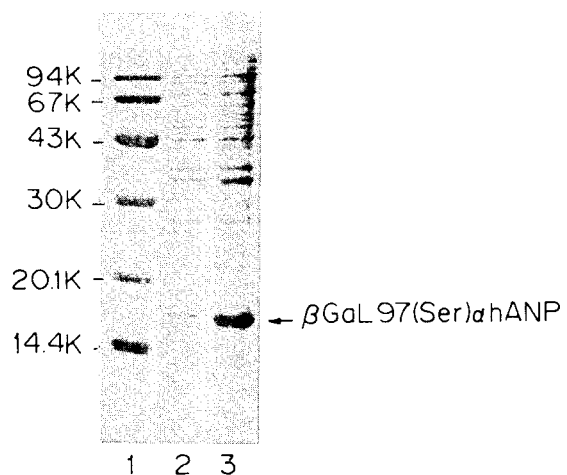
FIG. 4 shows a result of SDS-polyacrylamide gel electrophoresis (SDS-PAGE) of expression products from the plasmids pGHα97(Ser)rop⁻ (lane 2) and pGHα97S (lane 3), representing effects on the fusion protein production by removal of 3'-non-coding region of α-hANP gene and introduction of trp a immediately downstream of the α-hANP gene.
Figure 8:
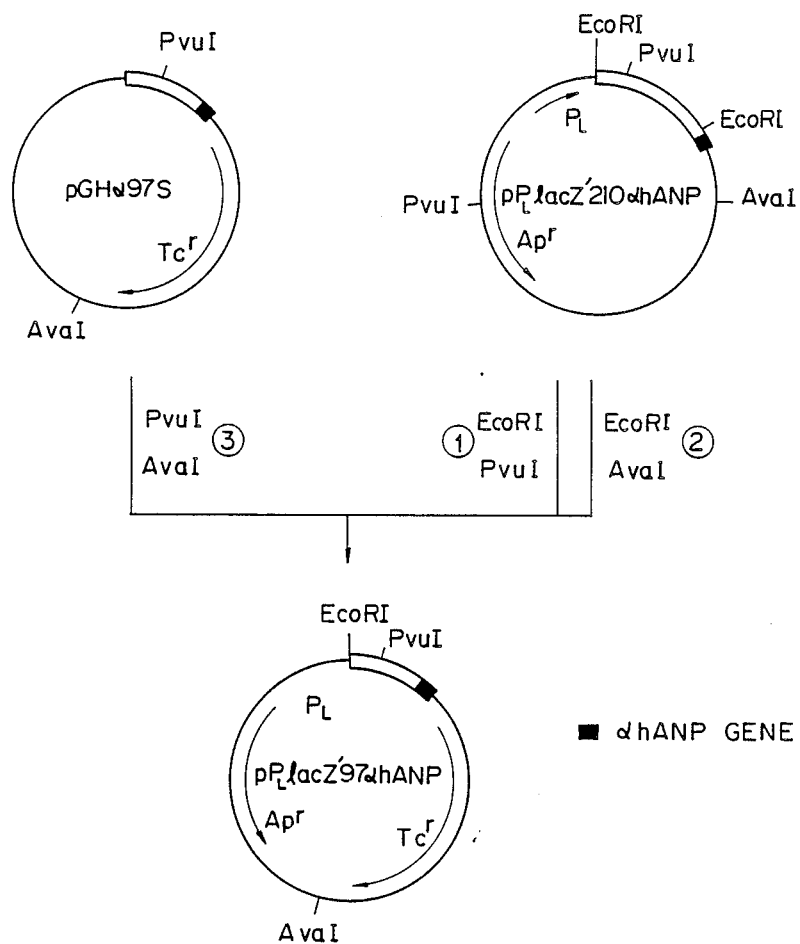
FIG. 8 represents a process for the construction of an expression plasmid pP$_L$lacZ'97(Ser)αhANP, which expresses a fusion protein under the control of a p$_L$ promoter of the λ phage.
Figure 9:
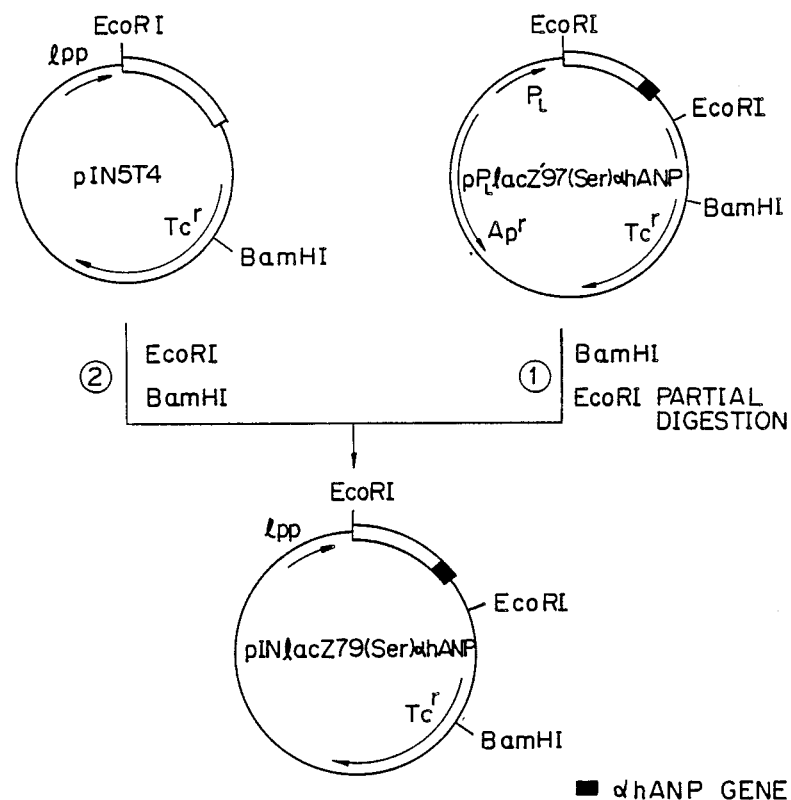
FIG. 9 represents a process for the construction of an expression plasmid pINlacZ'97(Ser)αhANP, which expresses a fusion protein under the control of an E. coli lpp promoter.

Ten μg of the plasmid pP$_L$lacZ'210αhANP constructed in FIG. 4 was digested completely with 50 units of EcoRI and 50 units of PvuI in 100 μl of H buffer at 37° C. for 60 minutes, the reaction mixture was subjected to 5% acrylamide gel electrophoresis to separate and purify a 143 bp DNA fragment containing lacZ' gene coding for N-terminal of β-galactosidase (No. 1 fragment in FIG. 8). Moreover, 3 μg of pP$_L$lacZ'2-10αhANP was digested completely with 20 units of EcoRI and 20 units of AvaI in 50 μl of H buffer at 37° C. for 60 minutes, and the largest DNA fragment containing P$_L$ promoter and ampicillin resistant gene (No. 2 fragment in FIG. 8) was electrophoretically separated and purified. On the other hand, 3 μg of pGHα97S was digested completely with 10 units of PvuI and 10 units of AvaI in 50 μl of H buffer, and a DNA fragment containing α-hANP gene and tetracycline resistant gene (No. 3 fragment in FIG. 8) was obtained.

These three DNA fragment were ligated by the same procedures described above, and the ligation mixture was used to transform E. coli W3110/C$_1$ (E. coli W3110 containing plasmid having C$_1$875 gene and kanamycin resistant gene). Tetracycline, ampicillin and kanamycin resistant clones were obtained. Plasmids from the clones were analyzed in a conventional manner to select desired plasmid pP$_L$lacZ'97(Ser)αhANP.

Example 6. Construction of pINlacZ'97(Ser)αhANP

Plasmid pINlacZ'97(Ser)αhANP was constructed by replacing P$_L$ promoter in plasmid pP$_L$lacZ'97(Ser)αhANP by lpp promoter of E. coli outer membrane lipoprotein gene.

Ten μg of pP$_L$lacZ'97(Ser)αhANP was digested completely with 50 units of BamHI in 100 μg of H buffer at 37° C. for 60 minutes, and then partially digested with 5 units of EcoRI, and the digestion product was subjected to 1% agarose gel electrophoresis to separate and purify a 809 bp EcoRI-BamHI DNA fragment containing βgal97(Ser)αhANP gene and a promotor region of tetracycline resistant gene (No. 1 fragment in FIG. 9). On the other hand, 3 μg of plasmid pIN5T4 was digested completely with 20 units of EcoRI and 20 units of BamHI in 50 μl of H buffer at 37° C. for 60 minutes, and the largest DNA fragment containing lpp promoter (No. 2 fragment in FIG. 9) was electrophoretically separated and purified.

These two DNA fragments were ligated by the same procedure as described above, and the ligation mixture was used to transform E. coli W3110. Tetracycline resistant clones were obtained, and plasmids from the clones were analyzed in a conventional manner to obtain desired plasmid pINlacZ'97(Ser)αhANP.

Example 7. Purification of α-hANP

E. coli W3110/pGEα97S prepared in Example 3 was cultured in 20 liter of a medium containing 0.4% yeast extract, 0.4% $KH_2PO_4$, 0.4% $K_2HPO_4$, 0.3% $Na_2HPO_4$, 0.02% $NH_4Cl$, 0.12% $(NH_4)_2SO_4$, 0.1% $MgSO_4 \cdot 7H_2O$, 1.5% glucose, 2% glycerine (added 4 times) (pH 7.0) supplemented with tetracycline in a 30 liter jar fermenter, at 37° C. for 18 hours with aeration and agitation. The culture broth was subjected to a high pressure homogenization (Manton Gaulin Laboratory Homogenizer 15M-8TA) at 8000 psi to disrupt the cells. The homogenate was centrifuged to obtain precipitate containing fusion protein, which was then washed with 10 mM Tris-HCl (pH 9.3) buffer. The washed precipitate was solubilized in 8 M urea solution. To the urea solution, 27 mM Tris-HCl (pH 9.3) was added to bring the urea concentration to 5 M. This urea solution was treated with 40 AU of API (Wako Junyaku, Japan) at 30° C. for 60 minutes, and the reaction mixture was filtered through a cartridge filter CWSC (Nippon Milipore Ltd.).

Next, the filtrate was chromatographed through Zeta prep QAE column (Nippon Milipore Ltd.) which adsorbs liberated βgal97(Ser), and intact βgal97(Ser)αhANP through βgal97(Ser) portion. A flow-through fraction containing liberated βgal97(SER) was obtained, and this fraction was adjusted to pH 5.0 by adding acetic acid. Next, the fraction was applied CM Toyopearl 650M column equilibrated with 5 M urea in 10 mM ammonium formate (pH 5.0). α-hANP was eluted stepwise with 225 mM NaCl and 400 mM NaCl to obtain a fraction containing α-hANP. The α-hANP fraction was applied to an SPW-C-ODS column (Chemco) in medium performance liquid chromatography (MPLC) (Murayama Kagaku) to desalt. Finally α-hANP was purified by $C_{18}$-HPLC.

Figure 10:
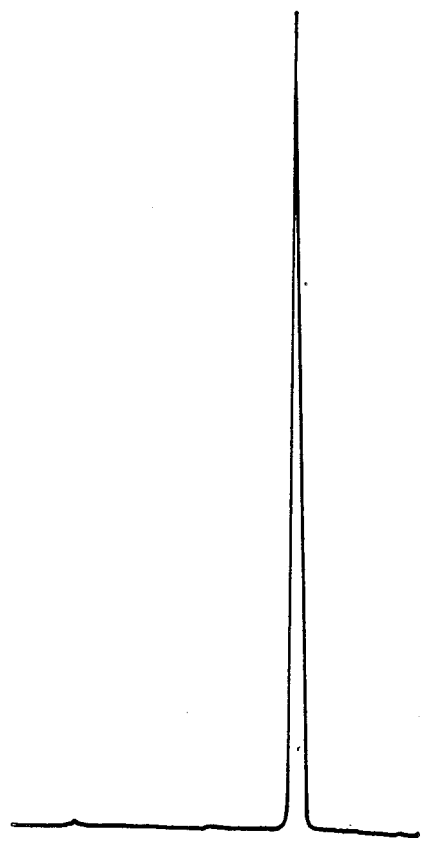
FIG. 10 shows an elution profile of reverse-phase high performance liquid chromatography (HPLC) for a target peptide α-hANP purified from a βgal 97(Ser)αhANP fusion protein.

The final α-hANP preparation provided a single peak in reverse HPLC (Waters) using YMC-A-302ODS column as shown in FIG. 10. Amino acid composition of the α-hANP preparation thus obtained, as determined by an amino acid autoanalyzer (Hitachi Seisakusho, 835-50) conformed to a value estimated from amino acid sequence of α-hANP. Moreover, amino acid sequence of the above-mentioned α-hANP preparation as determined by a gas phase protein sequencer Model 470A (Applied Biosystem) was the same as that of α-hANP.

Moreover the α-hANP preparation prepared by the present process was equivalent to a chemically synthesized α-hANP preparation (Peptide Research) in (1) natriuretic and blood pressure-lowering actions in SD rat, (2) relaxation activity on chick rectal tissue, and (3) cross-immunoreactivity in radioimmunoassay.

According to the present process, about 5 g of fusion protein (corresponding to about 1 g of α-hANP) is obtained from 1 liter of culture broth, and recovery and purification yield is about 50% to obtain α-hANP in a pure form. Such a high productivity and high recovery are very advantageous in the industrial production of α-hANP.

Note, E. coli W3110/C₁/pP_LlacZ'97(Ser)αhANP, containing plasmid pP_LlacZ'97(Ser)αhANP constructed in Example 5, as well as E. coli W3110/pINlacZ'97(Ser)αhANP, containing plasmid pINlacZ'97(Ser)αhANP constructed in Example 6, produced an amount of fusion protein βgal97(Ser)αhANP corresponding to about 30% relating to the total proteins produced by the transformant, and the fusion protein isolated from the precipitation fraction.

Example 8. Construction of plasmid

A. pG97SHPCT construction of pG97S18

Five μg of plasmid pGHα97SE was completely digested with 12 units of EcoRI and 80 units of SalI in 100 μl of S buffer, and the largest DNA fragment (1) was isolated and purified by agarose gel electrophoresis. On the other hand, 5 μg of plasmid pGHα97SE was completely digested with 80 units of SalI in 100 μl of S buffer, and the second large DNA fragment (2) containing a promotor region of tetracyline resistance gene was isolated and purified by agarose gel electrophoresis. Moreover, 1 μg of plasmid pUC18 (Takara Shuzo) was completely digested with 12 units of EcoRI and 80 units of SalI in 100 μl of S buffer, and the reaction mixture was treated with phenol to inactivate the enzyme, and extracted with ethanol to eliminate the phenol and salts (3). The above-mentioned DNA fragments (1), (2), and (3) were mixed and ligated, and the ligation mixture was used to transform E. coli W3110, and tetracycline resistant clones were obtained. The clones were analyzed by a conventional procedure to select plasmid pG97S18 wherein an EcoRI-SalI DNA fragment coding for the α-hANP gene in pGHα97SE is replaced by an EcoRI-SalI DNA fragment of a poly linker region in pUC18 having the following formula:

EcoRI　　　　　　　　　　　BamHI　　　SalI
5' GAATTCGAGCTCGGTACCCGGGGATCCTCTAGAGTCGAC 3'
3' CTTAAGCTCGAGCCATGGGCCCCTAGGAGATCTCAGCTG 5'

Figure 19:
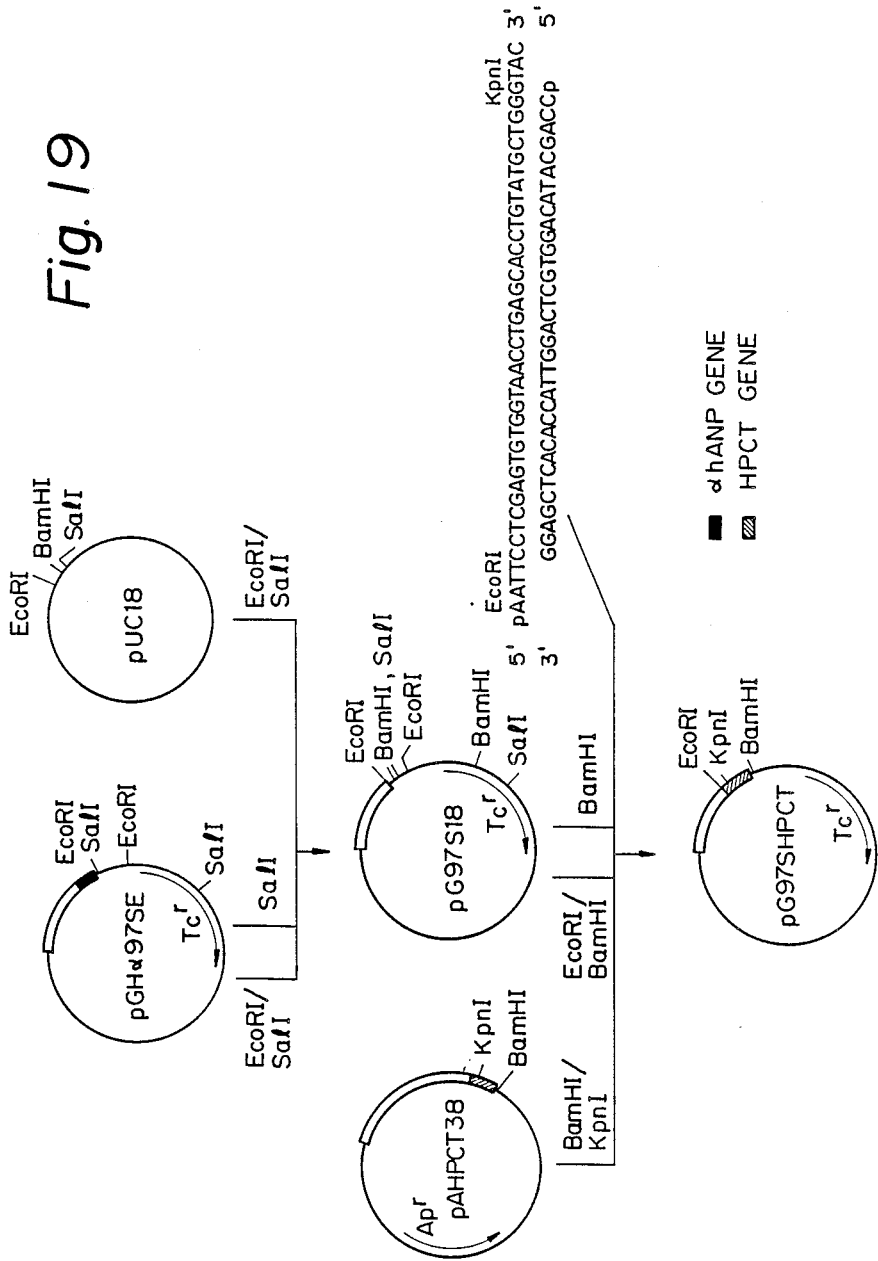
FIG. 19 represents a process for construction of plasmid pG97SHPCT.
Figure 20:
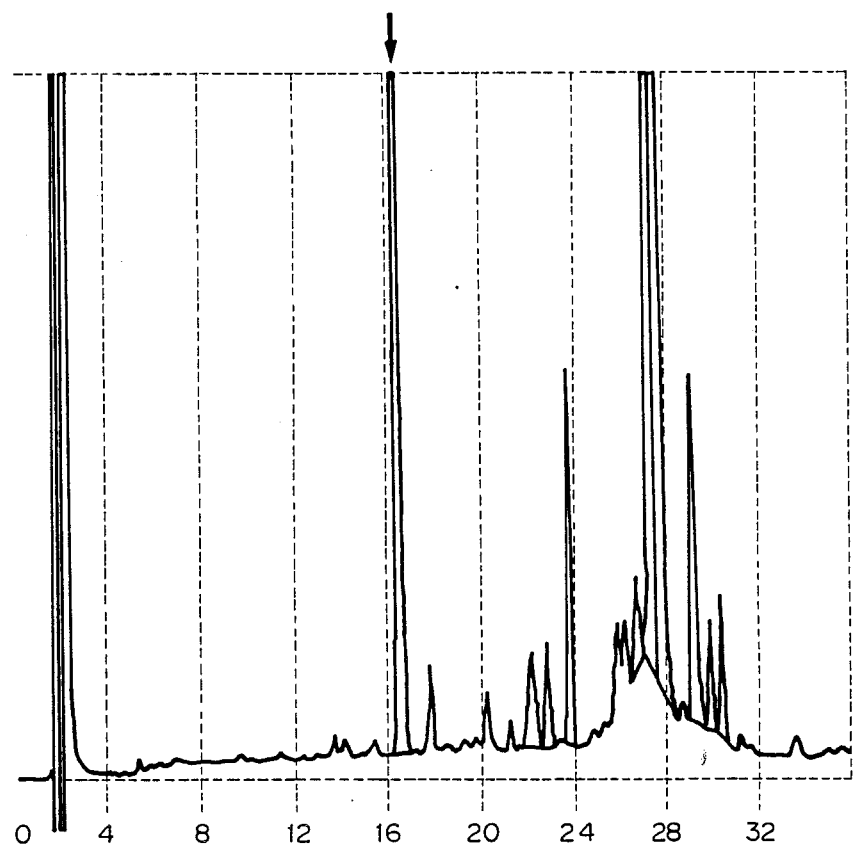
FIG. 20 represents the cleavage of a fusion protein βGal97SHPCT with protease V$_8$.

Five μg of plasmid pG97S18 was completely digested with 12 units of EcoRI and 12 units of BamHI in 50 μl of H buffer, and the largest DNA fragment (4) was separated and purified by agarose gel electrophoresis. On the other hand, 5 μg of plasmid pGH97S18 was completely digested with 12 units of βamHI in 50 μg of H buffer, and a DNA fragment (7) containing a tetracycline gene promotor was separated and purified by agarose gel electrophoresis. Moreover, 10 μg of plasmid pAHPCT38 was completely digested with 12 units of BamHI and 24 units of KpnI in M buffer, and 81 bp KpnI-BamHI DNA fragment (6) coding for from the seventh Tyr to 32nd Pro calculated from the N-terminal of calcitonin, followed by Gly-Lys-Lys-Arg was separated and purified by polyacrylamide gel electrophoresis. On the other hand, a double stranded oligonucleotide (7) having the following sequence:

and having EcoRI cohesive end and KpnI cohesive end was prepared. The above-mentioned DNA fragments (4), (5), (6), and (7) were mixed and ligated, and the ligation mixture was used to transform E. coli W3110 to obtain tetracycline resistant clones. These clones were analysed by a conventional process to obtain a desired plasmid pG97SHPCT (FIG. 19).

Note, the above-mentioned plasmid pAHPCT38 is described in detail in Japanese Unexamined Patent Publication No. 58-203953, and E. coli containing the plasmid pAHPCT38, i.e., Escherichia coli E15/pAHPCT38 designated as SBMC138 was deposited with the FRI as FERM P-6523 on June 10, 1982, and transferred to international deposition under the Budapest treaty as FERM BP-282 on May 2, 1983.

Example 9. Purification of human calcitonin precursor

E. coli W3110/pG97SHPCT transformed with the above-mentioned plasmid pG97SHPCT was cultured in a medium containing 0.5% glycerine, 2.4% yeast extreat, 1.2% trypton and 100 mM potassium-phosphate (pH 7.5) supplemented with tetracycline at 37° C. for 16 hours. Next, the culture broth was centrifuged to obtain bacterial cells, which were then suspended in 10 mM Tris-HCl (pH 7.8) buffer and disrupted with a French pressure cells and press (SLM-AMINCO) at 8000 psi. The disruptant was centrifuged at 1000 g for 10 minutes, to obtain both a supernatant and a precipitate, which were then analysed by SDS-PAGE. As a result, βGal97SHPCT was producted in approximately the same amount as βGal97SαhANP, and recovered in the precipitate fraction as in the case of βGal97SαhANP. This precipitate was suspended in 8 M aqueous urea solution, and to the suspension was added three volumes of 67 mM Tris-HCl (pH 7.8) to bring a concentration of urea to 2 M. To the diluted suspension was added protease V8 (Boehringer Mannheim) in an amount of 1/2000(W/W) relative to the substrate, and the whole was incubated at 37° C. for 10 minutes. An aliquot of the reaction mixture was analysed by reverse phase high performance liquid chromatography using YMC-A3020DS (Shimazu). As a result, it was observed that, among ten glutamic acid residues present in βGal97SHPCT a bond at a glutamic acid residue present between βGal97S and HPCT is most ready to be cleaved. Moreover, the reaction mixture was subjected to column chromatography using Zeta-Prep QAE equilibrated with 50 mM Tris-HCl (pH 7.8) buffer containing 2 M urea, and as a result, approximately 100% of HPCT was recovered in a flow-through fraction at a purity of about 95%.

This means that βGal97S is suitable as a partner protein not only for the productions of α-hANP but also for the production of human calcitanin precursor (HPCT).

We claim:

1. A process for production of a target peptide, comprising the steps of:
    (a) culturing Escherichia coli transformed with a plasmid capable of expressing a fusion protein under control of a promoter of E. coli origin or a promoter of phage origin, wherein the fusion protein is represented by the following formula:

A—L—B wherein

B represents the target peptide; A represents a partner polypeptide which is a part of an E. coli β-galactosidase protein from the first amino acid residue to the 97th amino acid residue wherein cysteine at the 76th position in the β-galactosidase protein is replaced by a serine residue; and L represents a linker peptide having at its C-terminal a linker amino acid residue which linker peptide positions between a C-terminal of the partner polypeptide and an N-terminal of the target peptide wherein the same amino acid as the linker amino acid is not present in the target peptide, and the linker amino acid is selected so that the peptide bond between the C-terminal of the linker amino acid and the N-terminal of the target peptide is cleaved by a protease or the linker amino acid is selectively degraded by a chemical substance;
    (b) disrupting the cultured cells and obtaining an insoluble fraction containing the fusion protein;
    (c) solubilizing the fusion protein with a solubilizing agent;
    (d) treating the solubilized fusion protein with a protease or a chemical substance to liberate the target peptide; and
    (e) isolating the target peptide; wherein the target peptide is selected from the group consisting of α-hANP having the following structure (I):

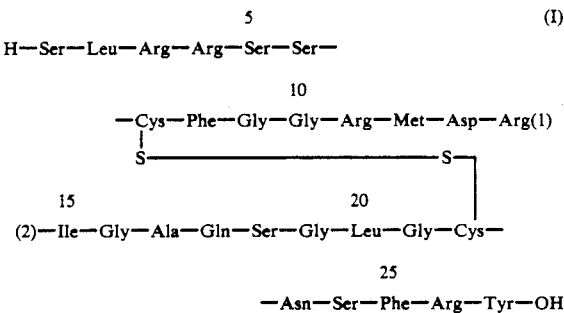

wherein (1) is directly bonded with (2), and a human calcitonin precursor (HPCT) having the following formula (II):

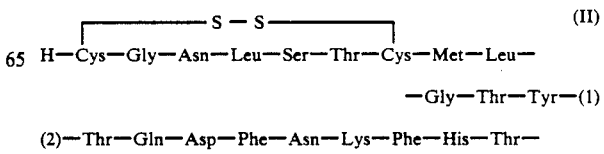

-continued $-$Phe$-$Pro$-$Gln$-$(3)

(4)$-$Thr$-$Ala$-$Ile$-$Gly$-$Val$-$Gly$-$Ala$-$Pro$-$Gly$-$ $-$Lys$-$Lys$-$Arg$-$OH wherein (1) is directly bonded with (2), and (3) is directly bonded with (4).

2. The process according to claim 1, wherein the promoter is selected from the group consisting of a promoter derived from a E. coli lactose gene, a $P_L$ promoter derived from a λ phage, and a lpp promoter derived from an E. coli outer membrane lipoprotein.

3. The process according to claim 1, wherein the plasmid is pHGα97(Ser)rop⁻.

4. The process according to claim 1, wherein the plasmid is pGHα97S.

5. The process according to claim 1, wherein the plasmid is pGHα97SE.

6. A physiologically active peptide produced according to claim 1.

* * * * *